US009073911B2

(12) United States Patent
Galley et al.

(10) Patent No.: US 9,073,911 B2
(45) **Date of Patent: *Jul. 7, 2015**

(54) PYRAZOLE DERIVATIVES

(75) Inventors: Guido Galley, Rheinfelden (DE); Cedric Ghellamallah, Huningue (FR); Roger Norcross, Olsberg (CH); Philippe Pflieger, Schwoben (FR)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 49 days.

This patent is subject to a terminal disclaimer.

(21) Appl. No.: 13/485,969

(22) Filed: Jun. 1, 2012

(65) Prior Publication Data

US 2012/0316172 A1 Dec. 13, 2012

(30) Foreign Application Priority Data

Jun. 9, 2011 (EP) .................................... 11169217

(51) Int. Cl.
*C07D 413/12* (2006.01)
*C07D 413/14* (2006.01)

(52) U.S. Cl.
CPC ............ *C07D 413/14* (2013.01); *C07D 413/12* (2013.01)

(58) Field of Classification Search
CPC ............................ C07D 413/14; C07D 419/14
USPC .............. 514/236.5, 406; 544/140; 548/364.1
See application file for complete search history.

(56) References Cited

U.S. PATENT DOCUMENTS

2011/0152245 A1* 6/2011 Groebke Zbinden et al. ........................ 514/211.01

FOREIGN PATENT DOCUMENTS

| | | |
|---|---|---|
| WO | 97/12874 | 4/1997 |
| WO | 99/28300 | 6/1999 |
| WO | 02/076950 | 10/2002 |
| WO | 2011/057973 | 5/2011 |
| WO | 2011076678 | 6/2011 |
| WO | 2013/016879 | 2/2012 |
| WO | 2012/168265 | 12/2012 |

OTHER PUBLICATIONS

Patani et al. Bioisosterism: A Rational Approach in Drug Design. Chem. Rev. 96, 3147-3176 (1996).*
Branchek et al., "Curr Opin Pharmacol" 3:90-97 ( 2003).
Usdin et al., "Psychopharmacology Series" (Trace Amines and the Brain), 1:1-281 ( 1976).
Carlsson et al., "Annu. Rev. Pharmacol. Toxicol." 41:237-260 ( 2001).
Premont et al., "Proc. Natl. Acad. Sci. USA" 98:9474-9475 ( 2001).
Tuite et al., "Expert Opin. Investig. Drugs" 12:1335-1352 ( 2003).
McCormack et al., "J. Neurosci." 6:94-101 ( 1986).
Wong et al., "Research and Treatment Approaches to Depression. Nat. Rev. Neurosci." 2:343-351 ( 2001).
Castellanos et al., "Nat. Rev. Neurosci." 3:617-628 ( 2002).
Parker et al., "J. Pharmacol. Exp. Ther." 245:199-210 ( 1988).
Lindemann et al., "Genomics" 85:372-385 ( 2005).
Dyck, L. E., "Life Sci." 44:1149-1156 ( 1989).
Deutch et al. Neurotransmitters in Fundamental Neuroscience 2nd edition,Academic Press,:193-234 ( 1999).
Mousseau et al., "Prog. Brain Res." 106:285-291 ( 1995).
Lindemann et al., "Trends in Pharmacol. Sci." 26:274-281 ( 2005).
(International Search Report for PCT/EP2012/060627 Jul. 23, 2012).
The English translation of letter of opposition in the corresponding Costa Rican Application No. 2013-0582, which was notified by the Costa Rican Patent Office on May 23, 2014.
The English translation of the Japanese Office Action, issued on Jan. 13, 2015, in the related Japanese application No. 2014-514042.

* cited by examiner

*Primary Examiner* — Barbara P Badio
*Assistant Examiner* — Sara E Townsley

(57) ABSTRACT

The invention relates to compounds of formula IA and IB

IA and

IB wherein $R^1$, $R^2$, $R^3$, $R^4$ and Z are as defined herein or to a pharmaceutically suitable acid addition salt thereof. Compounds of formulas IA and IB have a good affinity to the trace amine associated receptors (TAARs), especially for TAAR1. The compounds can be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

4 Claims, No Drawings

PYRAZOLE DERIVATIVES

PRIORITY TO RELATED APPLICATION(S)

This application claims the benefit of European Patent Application No. 11169217.4, filed Jun. 9, 2011, which is hereby incorporated by reference in its entirety.

BACKGROUND OF THE INVENTION

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies[7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol.* 1*: Trace Amines and the Brain. [Proceedings of a Study Group at the* 14*th Annual Meeting of the American College of Neuropsychopannacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

SUMMARY OF THE INVENTION

The present invention provides compounds of formula IA and IB and their pharmaceutically acceptable salts, pharmaceutical compositions containing them, and methods for the manufacture of the compounds and compositions of the invention. The invention further provides methods for the treatment of diseases related to the biological function of the trace amine associated receptors. The invention provides methods for the control, treatment, or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The invention provides compounds of formula IA and IB

IA and

IB wherein $R^1$ is hydrogen, phenyl optionally substituted by halogen, CN or lower alkoxy, or lower alkoxy substituted by halogen;

$R^2$ is hydrogen or lower alkyl;

$R^3$ is hydrogen, lower alkyl, phenyl optionally substituted by one or more substituents selected from halogen, cyano and lower alkoxy substituted by halogen, pyridinyl optionally substituted by halogen or lower alkyl substituted by halogen, pyrimidinyl optionally substituted by lower alkyl substituted by halogen, or pyrazinyl optionally substituted by halogen, cyano or lower alkyl substituted by halogen;

$R^4$ is hydrogen, lower alkyl or phenyl; and

Z is a bond, —$CH_2$— or —O—;

or a pharmaceutically acceptable acid addition salt thereof.

The invention includes all racemic mixtures, all their corresponding enantiomers and/or optical isomers. In addition, all tautomeric forms of compounds of formula IA and IB are also encompassed by the present invention.

Compounds of formulas IA and IB have a good affinity to the trace amine associated receptors (TAARs), especially for TAAR1.

The compounds can be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety and attention deficit hyperactivity disorder (ADHD) and diabetes.

DETAILED DESCRIPTION OF THE INVENTION

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above which is attached via an oxygen atom.

The term "halogen" denotes chlorine, iodine, fluorine and bromine.

As used herein, the term "lower alkoxy substituted by halogen" denotes an alkoxy group as defined above and wherein at least one hydrogen atom is replaced by halogen.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The terms "pharmaceutically acceptable carrier" and "pharmaceutically acceptable auxiliary substance" refer to carriers and auxiliary substances such as diluents or excipients that are compatible with the other ingredients of the formulation.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

One embodiment of the invention is compounds of formula IA-1

IA-1 wherein

R is hydrogen, halogen, CN, lower alkoxy or lower alkoxy substituted by halogen;

$R^2$ is hydrogen or lower alkyl;

$R^3$ is hydrogen or lower alkyl;

Z is a bond, —$CH_2$— or —O—; and n is 1 or 2; wherein when n=2, each R is independently defined;

or a pharmaceutically suitable acid addition salt thereof, for example the following compounds:

(S)—N-(4-(morpholin-2-yl)phenyl)-5-phenyl-1H-pyrazole-3-carboxamide, (S)-1-methyl-N-(4-(morpholin-2-yl)phenyl)-5-phenyl-1H-pyrazole-3-carboxamide, (S)-5-(3-cyanophenyl)-N-(4-(morpholin-2-yl)phenyl)-1H-pyrazole-3-carboxamide, (S)-5-(3-cyanophenyl)-4-methyl-N-(4-(morpholin-2-yl)phenyl)-1H-pyrazole-3-carboxamide, (S)-5-(5-cyano-2-fluorophenyl)-N-(4-(morpholin-2-yl)phenyl)-1H-pyrazole-3-carboxamide, (S)-5-(3-cyano-4-fluorophenyl)-N-(4-(morpholin-2-yl)phenyl)-1H-pyrazole-3-carboxamide, and (S)-5-(3-(difluoromethoxy)phenyl)-1-ethyl-N-(4-(morpholin-2-yl)phenyl)-1H-pyrazole-3-carboxamide.

One further embodiment of the invention is compounds of formula IB-1

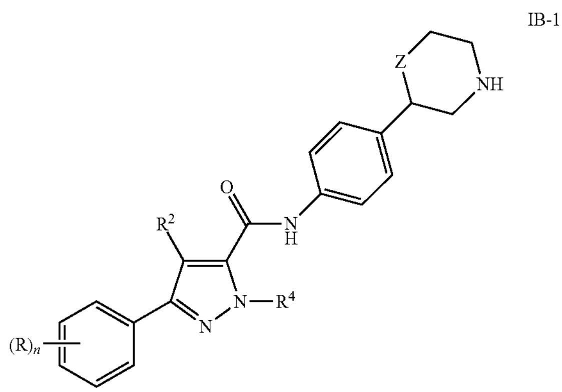

wherein

R is hydrogen, halogen, CN, lower alkoxy or lower alkoxy substituted by halogen;

$R^2$ is hydrogen or lower alkyl;

$R^4$ is hydrogen or lower alkyl;

Z is a bond, —$CH_2$— or —O—; and n is 1 or 2; wherein when n=2, each R is independently defined;

or a pharmaceutically acceptable acid addition salt thereof, for example the following compounds:

(S)-3-(3-chlorophenyl)-N-(4-(morpholin-2-yl)phenyl)-1H-pyrazole-5-carboxamide, (S)-3-(4-fluorophenyl)-N-(4-(morpholin-2-yl)phenyl)-1H-pyrazole-5-carboxamide, (S)-3-(3-methoxyphenyl)-N-(4-(morpholin-2-yl)phenyl)-1H-pyrazole-5-carboxamide, (S)-1-methyl-N-(4-(morpholin-2-yl)phenyl)-3-phenyl-1H-pyrazole-5-carboxamide, (S)-4-methyl-N-(4-(morpholin-2-yl)phenyl)-3-phenyl-1H-pyrazole-5-carboxamide, (S)-3-(4-methoxyphenyl)-N-(4-(morpholin-2-yl)phenyl)-1H-pyrazole-5-carboxamide, (S)-3-(2-fluorophenyl)-N-(4-(morpholin-2-yl)phenyl)-1H-pyrazole-5-carboxamide, (S)-3-(2-methoxyphenyl)-N-(4-(morpholin-2-yl)phenyl)-1H-pyrazole-5-carboxamide, (S)-3-(2-chlorophenyl)-N-(4-(morpholin-2-yl)phenyl)-1H-pyrazole-5-carboxamide, (S)-3-(3,4-dimethoxyphenyl)-N-(4-(morpholin-2-yl)phenyl)-1H-pyrazole-5-carboxamide, (R)-3-(4-chlorophenyl)-N-(4-(morpholin-2-yl)phenyl)-1H-pyrazole-5-carboxamide, (R)-3-(2-chlorophenyl)-N-(4-(morpholin-2-yl)phenyl)-1H-pyrazole-5-carboxamide, (S)-3-(4-chlorophenyl)-N-(4-(morpholin-2-yl)phenyl)-1H-pyrazole-5-carboxamide, (R)-3-(3-chlorophenyl)-N-(4-(morpholin-2-yl)phenyl)-1H-pyrazole-5-carboxamide, (R)-3-(3-methoxyphenyl)-N-(4-(morpholin-2-yl)phenyl)-1H-pyrazole-5-carboxamide, (S)-3-(3-chlorophenyl)-1-methyl-N-(4-(morpholin-2-yl)phenyl)-1H-pyrazole-5-carboxamide, (R)-1-methyl-N-(4-(morpholin-2-yl)phenyl)-3-phenyl-1H-pyrazole-5-carboxamide, (S)-3-(4-cyanophenyl)-1-methyl-N-(4-(morpholin-2-yl)phenyl)-1H-pyrazole-5-carboxamide, (S)-3-(4-fluorophenyl)-1-methyl-N-(4-(morpholin-2-yl)phenyl)-1H-pyrazole-5-carboxamide, (S)-3-(3-methoxyphenyl)-1-methyl-N-(4-(morpholin-2-yl)phenyl)-1H-pyrazole-5-carboxamide, (S)-3-(3-cyanophenyl)-1-methyl-N-(4-(morpholin-2-yl)phenyl)-1H-pyrazole-5-carboxamide, (S)-3-(3-cyanophenyl)-1-ethyl-N-(4-(morpholin-2-yl)phenyl)-1H-pyrazole-5-carboxamide, (S)-3-(4-cyanophenyl)-1-ethyl-N-(4-(morpholin-2-yl)phenyl)-1H-pyrazole-5-carboxamide, (S)-3-(3-cyanophenyl)-N-(4-(piperidin-3-yl)phenyl)-1H-pyrazole-5-carboxamide, (R)-3-(3-cyanophenyl)-N-(4-(piperidin-3-yl)phenyl)-1H-pyrazole-5-carboxamide, (rac) 3-(3-cyanophenyl)-N-(4-(pyrrolidin-3-yl)phenyl)-1H-pyrazole-5-carboxamide, (S)-3-(3-(difluoromethoxy)phenyl)-N-(4-(morpholin-2-yl)phenyl)-1H-pyrazole-5-carboxamide, (S)-3-(3-(difluoromethoxy)phenyl)-1-ethyl-N-(4-(morpholin-2-yl)phenyl)-1H-pyrazole-5-carboxamide, (S)-3-(3-cyano-2-fluorophenyl)-N-(4-(morpholin-2-yl)phenyl)-1H-pyrazole-5-carboxamide, and (S)-3-(3-(difluoromethoxy)phenyl)-1-methyl-N-(4-(morpholin-2-yl)phenyl)-1H-pyrazole-5-carboxamide.

One embodiment of the invention is compounds of formula IA-2,

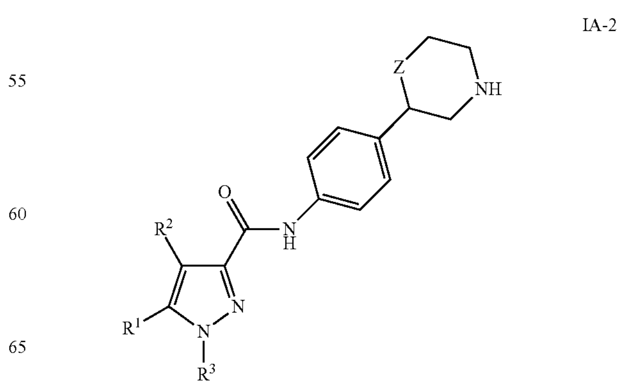

$R^1$ is hydrogen;

$R^2$ is hydrogen or lower alkyl;

$R^3$ phenyl optionally substituted by one or more substituents, selected from halogen, cyano and lower alkoxy substituted by halogen,
- pyridinyl optionally substituted by halogen or lower alkyl substituted by halogen,
- pyrimidinyl optionally substituted by lower alkyl substituted by halogen, or
- pyrazinyl optionally substituted by halogen, cyano or lower alkyl substituted by halogen; and Z is a bond, —$CH_2$— or —O—;

or a pharmaceutically suitable acid addition salt thereof, for example the following compounds:

(S)-1-(4-fluorophenyl)-N-(4-(morpholin-2-yl)phenyl)-1H-pyrazole-3-carboxamide, (R)-1-(4-fluorophenyl)-N-(4-(morpholin-2-yl)phenyl)-1H-pyrazole-3-carboxamide, (S)-1-(5-chloropyridin-2-yl)-N-(4-(morpholin-2-yl)phenyl)-1H-pyrazole-3-carboxamide, (S)—N-(4-(morpholin-2-yl)phenyl)-1-(5-(trifluoromethyl)pyridin-2-yl)-1H-pyrazole-3-carboxamide, (S)-1-(4-cyanophenyl)-N-(4-(morpholin-2-yl)phenyl)-1H-pyrazole-3-carboxamide, (R)—N-(4-(morpholin-2-yl)phenyl)-1-(5-(trifluoromethyl)pyridin-2-yl)-1H-pyrazole-3-carboxamide, (S)-1-(4-(difluoromethoxy)phenyl)-N-(4-(morpholin-2-yl)phenyl)-1H-pyrazole-3-carboxamide, (R)-1-(4-(difluoromethoxy)phenyl)-N-(4-(morpholin-2-yl)phenyl)-1H-pyrazole-3-carboxamide, (S)—N-(4-(morpholin-2-yl)phenyl)-1-(5-(trifluoromethyl)pyrimidin-2-yl)-1H-pyrazole-3-carboxamide, (S)-1-(6-chloropyrazin-2-yl)-N-(4-(morpholin-2-yl)phenyl)-1H-pyrazole-3-carboxamide, (S)-1-(3-chloropyrazin-2-yl)-N-(4-(morpholin-2-yl)phenyl)-1H-pyrazole-3-carboxamide, (S)-1-(5-chloropyrazin-2-yl)-N-(4-(morpholin-2-yl)phenyl)-1H-pyrazole-3-carboxamide, (S)—N-(4-(morpholin-2-yl)phenyl)-1-(6-(trifluoromethyl)pyrimidin-4-yl)-1H-pyrazole-3-carboxamide, (S)—N-(4-(morpholin-2-yl)phenyl)-1-(6-(trifluoromethyl)pyrazin-2-yl)-1H-pyrazole-3-carboxamide, (S)-1-(5-cyanopyrazin-2-yl)-N-(4-(morpholin-2-yl)phenyl)-1H-pyrazole-3-carboxamide, and (S)—N-(4-(morpholin-2-yl)phenyl)-1-(2-(trifluoromethyl)pyrimidin-4-yl)-1H-pyrazole-3-carboxamide.

One further embodiment of the invention is compounds of formula IB-2,

IB-2

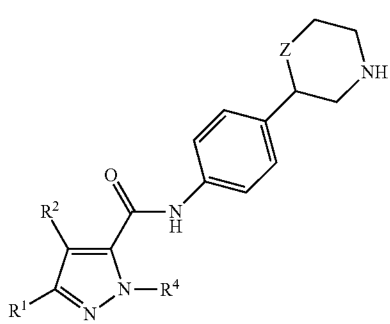

wherein $R^1$ is hydrogen;

$R^2$ is hydrogen or lower alkyl;

$R^4$ is hydrogen, lower alkyl or phenyl; and

Z is a bond, —$CH_2$— or —O—;

or a pharmaceutically suitable acid addition salt thereof, for example the following compound (S)—N-(4-(morpholin-2-yl)phenyl)-1-phenyl-1H-pyrazole-5-carboxamide.

The present compounds of formula IA and IB and their pharmaceutically acceptable salts can be prepared by methods known in the art, for example, by processes described below, which process comprises a) cleaving off the N-protecting group from compounds of formula

4-A

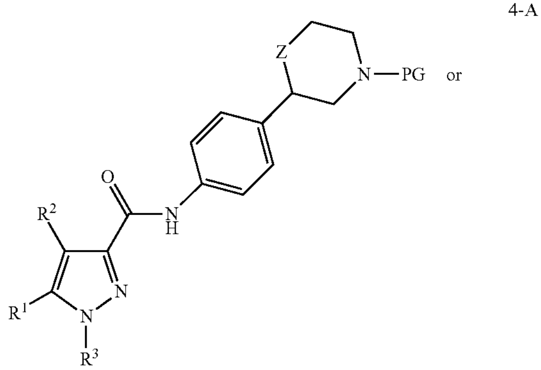

4-B

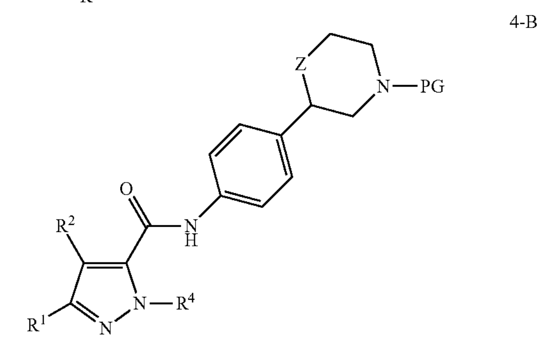

to form a compound of formula

IA

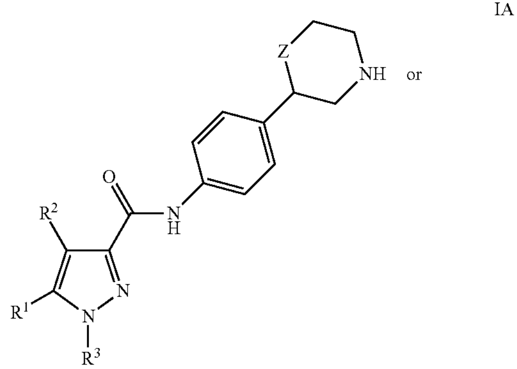

IB

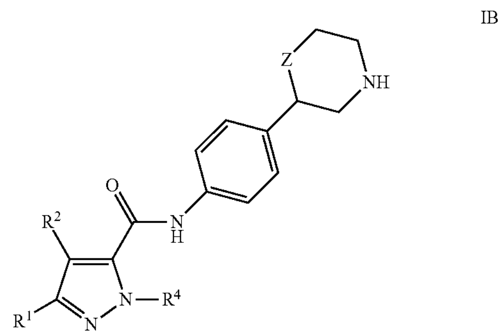

wherein PG is a N-protecting group selected from —C(O)O-tert-butyl and the other definitions are as described above, and, if desired, converting the compounds obtained into pharmaceutically acceptable acid addition salts.

The preparation of compounds of formula IA and IB of the present invention can be carried out in sequential or convergent synthetic routes. Syntheses of the compounds of the invention are shown in the following schemes 1 to 3 and in the description of 54 specific examples. The skills required for carrying out the reactions and purification of the resulting products are known to those skilled in the art. The substituents and indices used in the following description of the processes have the significance given herein before unless indicated to the contrary.

In more detail, the compounds of formula IA and IB can be manufactured by the methods given below, by the methods given in the examples or by analogous methods. Appropriate reaction conditions for the individual reaction steps are known to a person skilled in the art. The reaction sequence is not limited to the one displayed in schemes 1 to 3, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

GENERAL PROCEDURE

Scheme 1

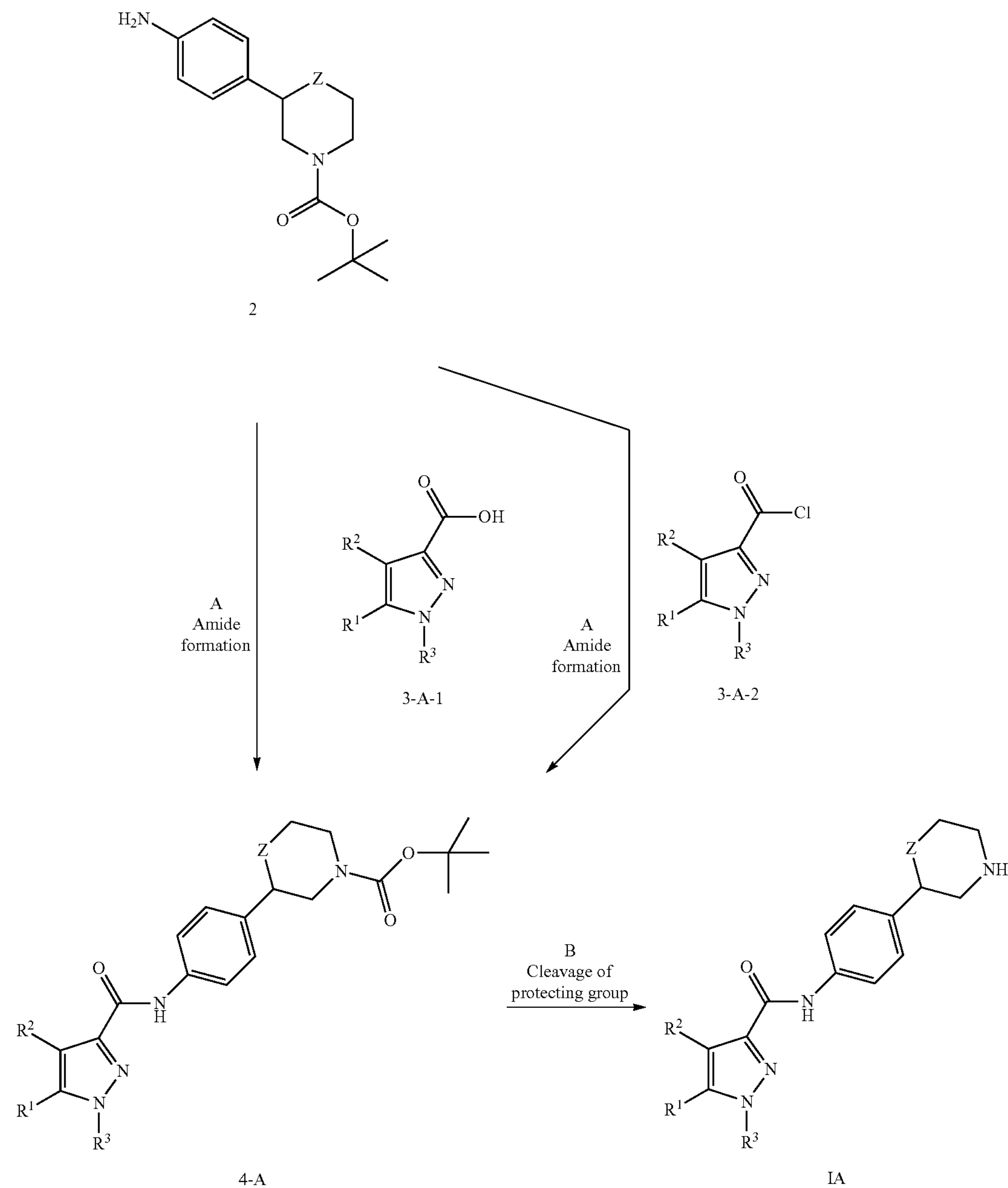

-continued

For examples using

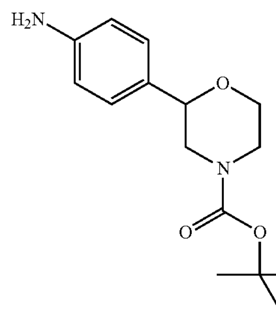

2-a

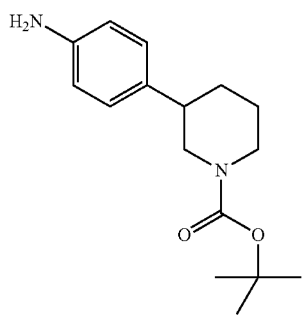

2-b

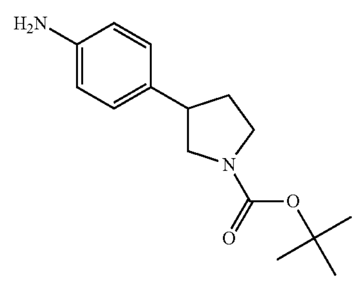

2-c

The substituents are as described above.

Step A: Amide formation can be accomplished by a coupling reaction between an amine 2 and acid chloride compounds 3-A-2 in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine. Examples of appropriate amines 2 include N-protected morpholine derivatives such as 2-a [CAS 1002726-96-6], piperidine derivatives such as 2-b [CAS 875798-79-1], pyrrolidine derivatives such as 2-c [CAS 908334-28-1].

Preferred conditions are triethylamine in THF at room temperature for 18 hours. Alternatively, amide formation can be accomplished by a coupling reaction between an amine 2 and carboxylic acids 3-A-1 in the presence of a coupling reagent such as DCC, EDC, TBTU, HBTU or HATU in the presence of an organic base such as triethylamine, N,N-diisopropylethylamine or N-methylmorpholine in halogenated solvents such as DMF, dichloromethane or 1,2-dichloroethane or ethereal solvents such as diethyl ether, dioxane, THF, DME or TBME.

Preferred conditions are HBTU with N-methylmorpholine in DMF at 60° C. for 18 hours. Step B: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, Dioxane, MeOH, EtOH or $H_2O$ at 0 to 80° C. Preferred conditions are HCl in dioxane at 60° C. for 1-20 h.

Scheme 2

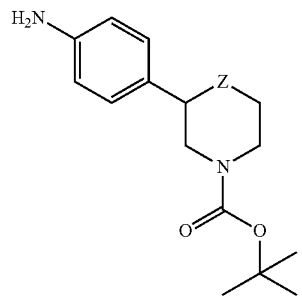

2

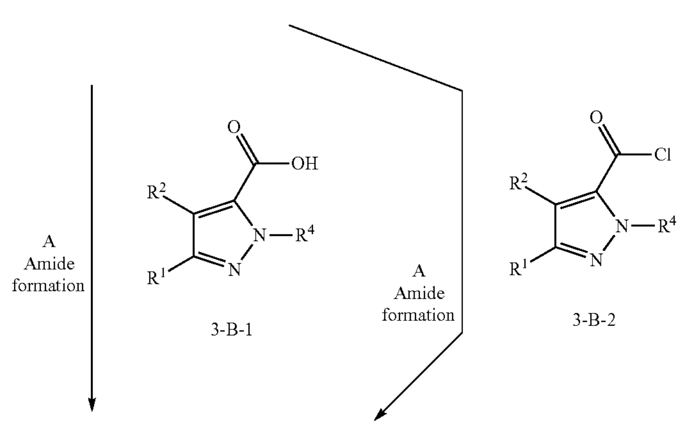

-continued
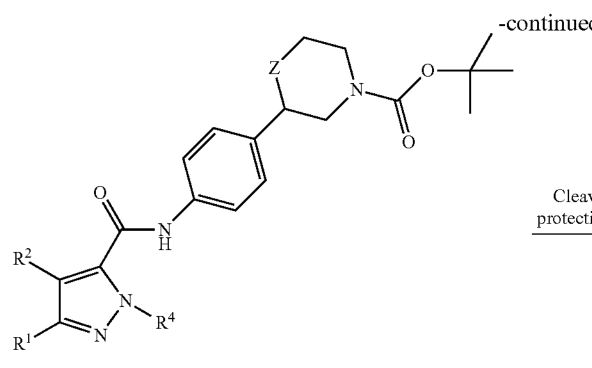
4-B
B
Cleavage of
protecting group
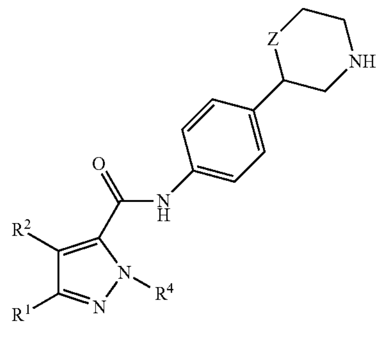
IB
For examples using
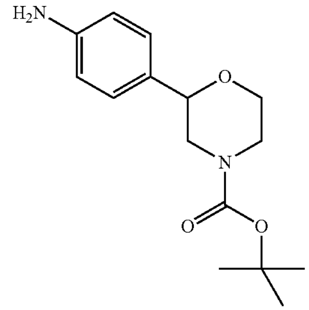
2-a
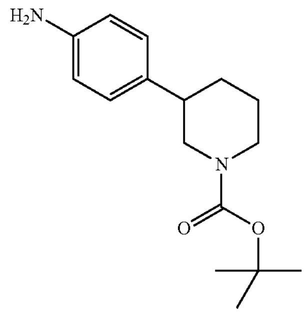
2-b
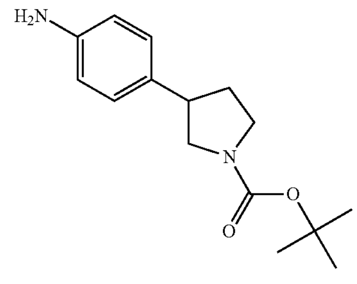
2-c
The process conditions are the same as described for scheme 1.
Scheme 3
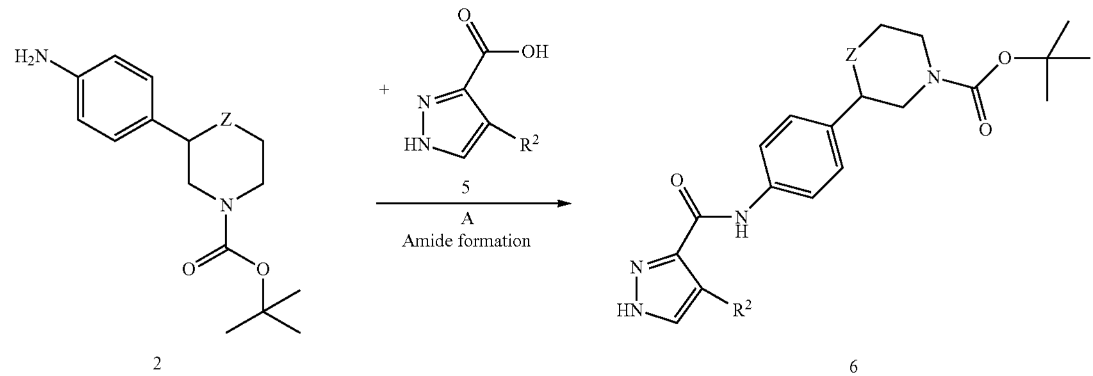
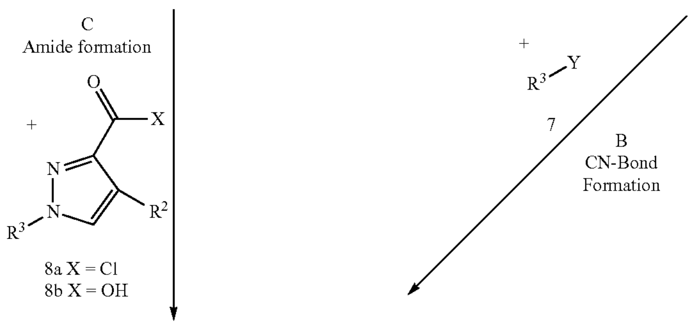

-continued

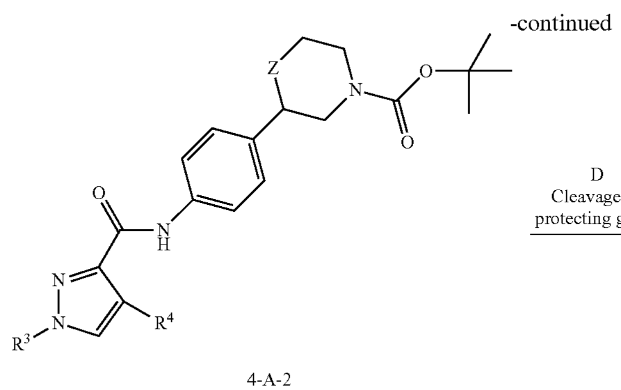

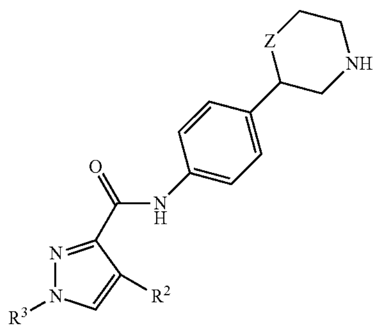

wherein

Y is halogen, $R^2$ is hydrogen or lower alkyl; $R^3$ is phenyl optionally substituted by one or more substituents, selected from halogen, cyano and lower alkoxy substituted by halogen, or is pyridinyl, optionally substituted by halogen or lower alkyl substituted by halogen, or is pyrimidinyl, optionally substituted by lower alkyl substituted by halogen, or is pyrazinyl, optionally substituted by halogen, cyano or lower alkyl substituted by halogen; and Z is a bond, —$CH_2$— or —O—;

Step A: Formation of amide 6 can be accomplished by a coupling reaction between an amine 2 and 1H-pyrazole-3-carboxylic acid 5 using a selective coupling reagent such as 4-(4,6-dimethoxy-1,3,5-triazin-2-yl)-4-methylmorpholinium chloride in a solvent such as methanol, ethanol or isopropanol at temperatures of 0° C. to 50° C. for 1 h to 24 hrs.

Preferred conditions are the use of 4-(4,6-dimethoxy-1,3,5-triazin-2-yl)-4-methylmorpholinium chloride in methanol for 1 h at 0° C. followed by 18 hours stirring at room temperature.

Examples of appropriate amines 2 include N-protected morpholine derivatives such as 2-a [CAS 1002726-96-6], piperidine derivatives such as 2-b [CAS 875798-79-1], pyrrolidine derivatives such as 2-c [CAS 908334-28-1].

Step B: C—N bond formation can be accomplished by treatment of aryl halide 7 or heteroaryl halide 7 with pyrazole 6 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos) and caesium carbonate in dioxane in a sealed tube heated at 100° C. overnight according to a modification of the procedure of van Leeuwen and co-workers (*Tetrahedron. Lett.* 1999, 40, 3789-3790).

In case the aryl halide 7 or heteroaryl halide 7 is activated towards undergoing nucleophilic substitution due to the presence of electron withdrawing substitutents, preferably by the presence of a trifluoromethylgroup, coupling with the pyrazole 6 can be achieved by reacting these compounds in the presence of a base such as diisopropylethylamine, triethylamine, potassium carbonate or sodium hydride in a solvent such as isopropanol, dioxane, dimethylsulfoxide, dimethylacetamide or dimethylformamide at a temperature between 50° C. and 140° C. for 1 hour to 24 hours.

Preferred conditions are heating the mixture of 6 and 7 with potassium carbonate in dimethylacetamide at 120° C. for 20 hours.

Step C: Amide formation can be accomplished by a coupling reaction between an amine 2 and acid chloride compounds 8a in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine Preferred conditions are triethylamine in THF at room temperature for 18 hours.

Alternatively, amide formation can be accomplished by a coupling reaction between an amine 2 and carboxylic acids 8b in the presence of a coupling reagent such as DCC, EDC, TBTU, HBTU or HATU in the presence of an organic base such as triethylamine, N,N-diisopropylethylamine or N-methylmorpholine in halogenated solvents such as DMF, dichloromethane or 1,2-dichloroethane or ethereal solvents such as diethyl ether, dioxane, THF, DME or TBME.

Preferred conditions are HBTU with N-methylmorpholine in DMF at 60° C. for 18 hours. Step D: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, Dioxane, MeOH, EtOH or $H_2O$ at 0 to 80° C. Preferred conditions are HCl in dioxane at 60° C. for 1-20 h.

The same general process as described in scheme 3 can be used for the preparation of compounds of formula IB-2.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula IA and IB

The compounds of formula IA and IB are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula IA and IB can be converted to the corresponding free bases by treatment with at least a stoichiometric equivalent of a suitable base such as sodium or potassium hydroxide, potassium carbonate, sodium bicarbonate, ammonia, and the like.

Example 1

(S)—N-(4-(morpholin-2-yl)phenyl)-5-phenyl-1H-pyrazole-3-carboxamide hydrochloride

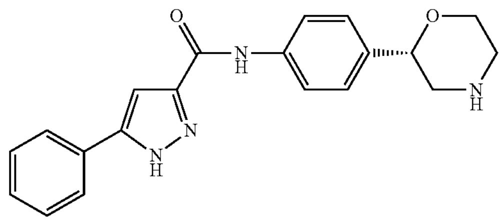 [SMILES: O=C(Nc1ccc([C@H]2CNCCO2)cc1)c1cc(-c2ccccc2)[nH]n1]

a) (S)-tert-butyl 2-(4-(5-phenyl-1H-pyrazole-3-carboxamido)phenyl)morpholine-4-carboxylate In a 25 mL round-bottomed flask, (S)-tert-butyl 2-(4-aminophenyl)morpholine-4-carboxylate (100 mg, 359 μmol, Eq: 1.00), 3-phenyl-1H-pyrazole-5-carboxylic acid (87.9 mg, 467 μmol, Eq: 1.3) (CAS-1134-49-2), N-Methylmorpholine (109 mg, 118 μl, 1.08 mmol, Eq: 3) and HBTU (204 mg, 539 μmol, Eq: 1.5) were combined with DMF (3.75 ml). The reaction mixture was stirred at 60° C. for 16.5 hours. The mixture was poured into water (10 ml) and extracted twice with EtOAc. The organic layers were washed with brine, dried over $MgSO_4$, filtered and concentrated in vacuo. The crude material was purified by column chromatography. (6 g silica gel (63-200A), eluent: heptane/EtOAc 2:1) to give the title compound as a white solid (120 mg, 74.5%). MS (ISP): 449.5 ($[M+H]^+$).

b) (S)—N-(4-(morpholin-2-yl)phenyl)-5-phenyl-1H-pyrazole-3-carboxamide hydrochloride To a solution of (S)-tert-butyl 2-(4-(5-phenyl-1H-pyrazole-3-carboxamido)phenyl)morpholine-4-carboxylate (120 mg, 268 μmol, Eq: 1.00) in dioxane (0.5 ml) was added 4M-HCl in dioxane (1.00 ml, 4.01 mmol, Eq: 15). The reaction mixture was stirred at 60° C. for 2 h. To the mixture was then added 10 ml of dioxane and the suspension was filtered off, washed with ether and dried under in high vacuum to give the target compound as a white solid (82.3 mg, 79.9%). MS (ISP): 349.2 ($[M+H]^+$).

Preparation of (S)-tert-butyl 2-(4-aminophenyl)morpholine-4-carboxylate

Step a) (S)-2-(4-Bromophenyl)morpholine 2.27 g (RS)-2-(4-Bromo-phenyl)-morpholine (CAS-1131220-82-0) were separated on a Chiralpak IA (8×32 cm) using n-Heptane/ethanol (1:11)+0.1% DEA.

(S)-2-(4-Bromo-phenyl)-morpholine: collected from 7.6 min to 9.4 min.

Yield 0.97 g (42.9%) with 97.4% ee (R)-2-(4-Bromo-phenyl)-morpholine: collected from 9.8 min to 13.9 min Yield 0.99 g (43.6%) with 97.4% ee Step b) (S)-tert-butyl 2-(4-bromophenyl)morpholine-4-carboxylate (S)-2-(4-Bromo-phenyl)-morpholine (36.3 g, 150 mmol) and N,N-diisopropylethylamine (23.3 g, 31.4 ml, 180 mmol) in THF (360 ml) were treated with di-tert-butyl dicarbonate (39.3 g, 180 mmol). The reaction mixture was stirred for 17 h at rt, concentrated in vacuo, diluted with ethyl acetate, washed with 1M-citric acid (2×100 ml), dried over magnesium sulfate, filtered and concentrated in vacuo. The crude material was crystallized from hexane to afford 47.1 g (92%) (S)-tert-butyl 2-(4-bromophenyl)morpholine-4-carboxylate as a off-white solid. MS (ISP): 344.1 ($[M+H]^+$).

Step c) (S)-tert-butyl 2-(4-(diphenylmethylene-amino)phenyl)morpholine-4-carboxylate (S)-tert-butyl 2-(4-bromophenyl)morpholine-4-carboxylate (47 g, 137 mmol), diphenylmethanimine (29.9 g, 27.6 m, 165 mmol), BINAP (6.41 g, 10.3 mmol) and $Pd_2(dba)_3$ (3.14 g, 3.43 mmol) were dissolved under Argon in dry and deaerated toluene (940 ml) and treated with sodium tert-butoxide (18.5 g, 192 mmol). The dark brown mixture was stirred at 90° C. for 18 h. The yellow/brown reaction mixture was diluted with toluene (700 ml), cooled to rt and extracted twice with water. The organic layer was separated, dried over magnesium sulfate and concentrated in vacuo. The crude product was diluted with 300 ml hexane, stirred for 1 h and filtered off, leading to an orange solid (68 g) which was purified by column chromatography (1.3 Kg silicagel, 20% ethylacetate/heptane). The combined and concentrated fractions were suspended in hexane, stirred for 17 h, filtered off andf dried in high vacuo, to yield 54.1 g (89%) yellow solid. MS (ISP): 443.3 ($[M+H]^+$).

Step d) (S)-tert-butyl 2-(4-aminophenyl)morpholine-4-carboxylate

A suspension of (S)-tert-butyl 2-(4-(diphenylmethylene-amino)phenyl)morpholine-4-carboxylate (54.1 g, 122 mmol), ammonium formate (116 g, 1.83 mol) and Pd/C 5% (6.5 g, 3.06 mmol) in methanol (930 ml) was stirred at 60° C. for 2 h. The reaction mixture was filtered and concentrated. The residue was dissolved in ethyl acetate and water. The organic phase was extracted twice with 0.5M HCl. The combined aqueous phases were basified with 2M-NaOH and extracted twice with DCM. The organic phases were dried over magnesium sulfate, filtered and dried in vacuo, to yield 31.95 g off-white solid. MS (ISP): 279.1 ([M+H]$^+$).

Example 2

(S)-3-(3-chlorophenyl)-N-(4-(morpholin-2-yl)phenyl)-1H-pyrazole-5-carboxamide hydrochloride

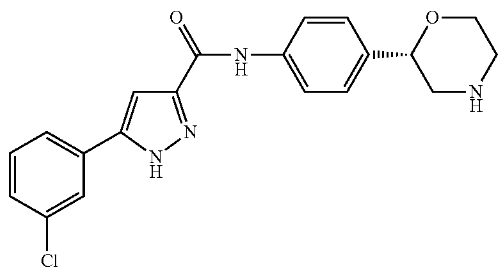 [SMILES: O=C(Nc1ccc([C@H]2CNCCO2)cc1)c1cc(-c2cccc(Cl)c2)[nH]n1]

The title compound was prepared in analogy to Example 1 using 5-(3-chloro-phenyl)-1H-pyrazole-3-carboxylic acid (CAS-595610-50-7) instead of 5-phenyl-1H-pyrazole-3-carboxylic acid. White solid. MS (ISP): 383.12 ([M+H]$^+$).

Example 3

(S)-3-(4-fluorophenyl)-N-(4-(morpholin-2-yl)phenyl)-1H-pyrazole-5-carboxamide hydrochloride

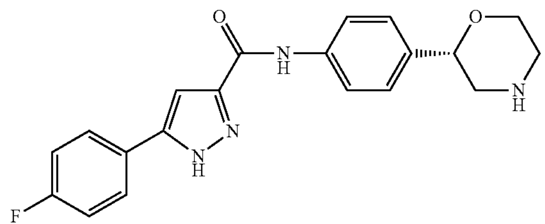 [SMILES: O=C(Nc1ccc([C@H]2CNCCO2)cc1)c1cc(-c2ccc(F)cc2)[nH]n1]

The title compound was prepared in analogy to Example 1 using 5-(4-fluoro-phenyl)-1H-pyrazole-3-carboxylic acid (CAS-870704-22-6) instead of 5-phenyl-1H-pyrazole-3-carboxylic acid. White solid. MS (ISP): 367.15 ([M+H]$^+$).

Example 4

(S)-3-(3-methoxyphenyl)-N-(4-(morpholin-2-yl)phenyl)-1H-pyrazole-5-carboxamide hydrochloride

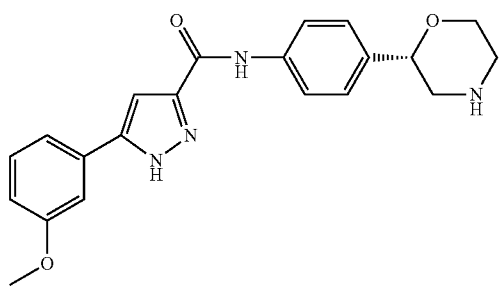 [SMILES: COc1cccc(-c2cc(C(=O)Nc3ccc([C@H]4CNCCO4)cc3)n[nH]2)c1]

The title compound was prepared in analogy to Example 1 using 5-(3-methoxy-phenyl)-1H-pyrazole-3-carboxylic acid (CAS-834868-54-1) instead of 5-phenyl-1H-pyrazole-3-carboxylic acid. White solid. MS (ISP): 379.17 ([M+H]$^+$).

Example 5

(S)-1-methyl-N-(4-(morpholin-2-yl)phenyl)-3-phenyl-1H-pyrazole-5-carboxamide hydrochloride

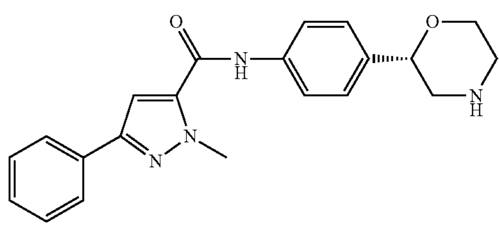 [SMILES: Cn1nc(-c2ccccc2)cc1C(=O)Nc1ccc([C@H]2CNCCO2)cc1]

The title compound was prepared in analogy to Example 1 using 1-Methyl-3-phenyl-1H-pyrazole-5-carboxylic acid (CAS-10250-64-3) instead of 5-phenyl-1H-pyrazole-3-carboxylic acid. White solid. MS (ISP): 363.18 ([M+H]$^+$).

Example 6

(S)-4-methyl-N-(4-(morpholin-2-yl)phenyl)-3-phenyl-1H-pyrazole-5-carboxamide hydrochloride

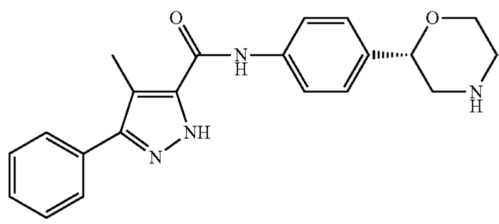 [SMILES: Cc1c(-c2ccccc2)n[nH]c1C(=O)Nc1ccc([C@H]2CNCCO2)cc1]

The title compound was prepared in analogy to Example 1 using 4-Methyl-5-phenyl-2H-pyrazole-3-carboxylic acid (CAS-879770-33-9) instead of 5-phenyl-1H-pyrazole-3-carboxylic acid. Off-white solid. MS (ISP): 363.5 ([M+H]$^+$).

Example 7

(S)-3-(4-methoxyphenyl)-N-(4-(morpholin-2-yl)phenyl)-1H-pyrazole-5-carboxamide hydrochloride

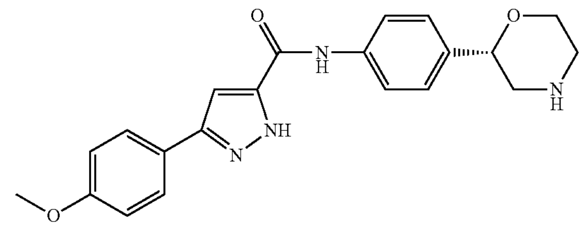 [SMILES: COc1ccc(-c2cc(C(=O)Nc3ccc([C@H]4CNCCO4)cc3)[nH]n2)cc1]

The title compound was prepared in analogy to Example 1 using 5-(4-methoxy-phenyl)-2H-pyrazole-3-carboxylic acid (CAS-27069-16-5) instead of 5-phenyl-1H-pyrazole-3-carboxylic acid. White solid. MS (ISP): 379.4 ([M+H]$^+$).

Example 8

(S)-3-(2-fluorophenyl)-N-(4-(morpholin-2-yl)phenyl)-1H-pyrazole-5-carboxamide hydrochloride

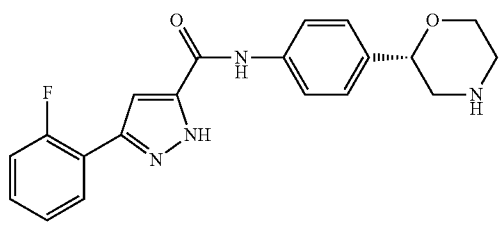 [SMILES: O=C(Nc1ccc([C@H]2CNCCO2)cc1)c1cc(-c2ccccc2F)n[nH]1]

The title compound was prepared in analogy to Example 1 using 5-(2-fluoro-phenyl)-2H-pyrazole-3-carboxylic acid (CAS-859155-87-6) instead of 3-phenyl-1H-pyrazole-5-carboxylic acid. White solid. MS (ISP): 367.1 ([M+H]$^+$).

Example 9

(S)-3-(2-methoxyphenyl)-N-(4-(morpholin-2-yl)phenyl)-1H-pyrazole-5-carboxamide hydrochloride

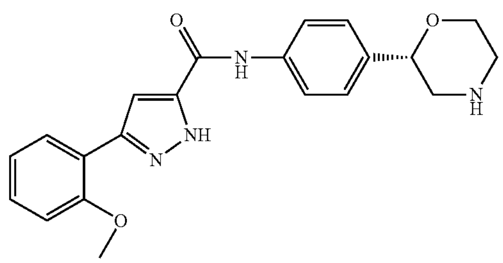 [SMILES: COc1ccccc1-c1cc(C(=O)Nc2ccc([C@H]3CNCCO3)cc2)[nH]n1]

The title compound was prepared in analogy to Example 1 using 5-(2-methoxy-phenyl)-2H-pyrazole-3-carboxylic acid (CAS-834868-54-1) instead of 3-phenyl-1H-pyrazole-5-carboxylic acid. White solid. MS (ISP): 379.4 ([M+H]$^+$).

Example 10

(S)-3-(2-chlorophenyl)-N-(4-(morpholin-2-yl)phenyl)-1H-pyrazole-5-carboxamide hydrochloride

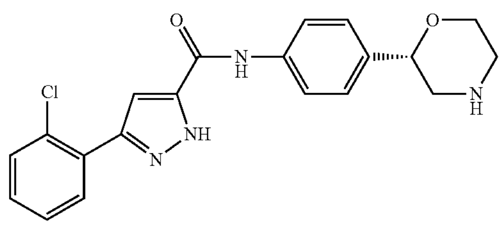 [SMILES: O=C(Nc1ccc([C@H]2CNCCO2)cc1)c1cc(-c2ccccc2Cl)n[nH]1]

The title compound was prepared in analogy to Example 1 using 3-(2-chlorophenyl)-1H-pyrazole-5-carboxylic acid (CAS-890621-13-3) instead of 3-phenyl-1H-pyrazole-5-carboxylic acid. White solid. MS (ISP): 383.2 ([M+H]$^+$).

Example 11

(S)-3-(3,4-dimethoxyphenyl)-N-(4-(morpholin-2-yl)phenyl)-1H-pyrazole-5-carboxamide hydrochloride

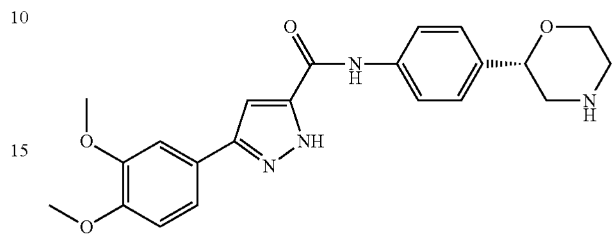

The title compound was prepared in analogy to Example 1 using 5-(3,4-dimethoxy-phenyl)-2H-pyrazole-3-carboxylic acid (CAS-909857-88-1) instead of 3-phenyl-1H-pyrazole-5-carboxylic acid. Off-white solid. MS (ISP): 409.3 ([M+H]$^+$).

Example 12

(R)-3-(4-chlorophenyl)-N-(4-(morpholin-2-yl)phenyl)-1H-pyrazole-5-carboxamide hydrochloride

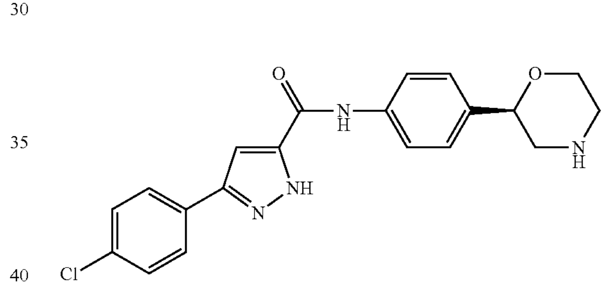

The title compound was prepared in analogy to Example 1 using (R)-tert-butyl 2-(4-aminophenyl)morpholine-4-carboxylate instead of (S)-tert-butyl 2-(4-aminophenyl)morpholine-4-carboxylate and 3-(4-chlorophenyl)-1H-pyrazole-5-carboxylic acid (CAS-54006-63-2) instead of 3-phenyl-1H-pyrazole-5-carboxylic acid. Off-white solid. MS (ISP): 383.1 ([M+H]$^+$).

Preparation of (R)-tert-butyl 2-(4-aminophenyl)morpholine-4-carboxylate

Step a) (R)-2-(4-Bromophenyl)morpholine 2.27 g (RS)-2-(4-Bromo-phenyl)-morpholine (CAS-1131220-82-0) were separated on a Chiralpak IA (8×32 cm) using n-Heptane/ethanol (1:11)+0.1% DEA. (S)-2-(4-Bromo-phenyl)-morpholine: collected from 7.6 min to 9.4 min. Yield 0.97 g (42.9%) with 97.4% ee.

(R)-2-(4-Bromo-phenyl)-morpholine: collected from 9.8 min to 13.9 min

Yield 0.99 g (43.6%) with 97.4% ee

Step b) (R)-tert-butyl 2-(4-bromophenyl)morpholine-4-carboxylate (R)-2-(4-Bromophenyl)morpholine (6 g, 24.8 mmol) and N,N-diisopropylethylamine (3.84 g, 5.19 ml, 29.7 mmol) in THF (60 ml) were treated with di-tert-butyl dicarbonate (6.49 g, 29.7 mmol). The reaction mixture was stirred for 17 h at rt, concentrated in vacuo, diluted with ethyl acetate, washed with 1M-citric acid, dried over magnesium sulfate, filtered and concentrated in vacuo. The crude material was crystallized from heptane/ethyl acetate to afford 8.48 g (87%) (R)-tert-butyl 2-(4-bromophenyl)morpholine-4-carboxylate as a white solid. MS (ISP): 344.1 ([M+H]$^+$).

Step c) (R)-tert-butyl 2-(4-(diphenylmethylene-amino)phenyl)morpholine-4-carboxylate (R)-tert-butyl 2-(4-bromophenyl)morpholine-4-carboxylate (5.4 g, 15.8 mmol), diphenylmethanimine (3.43 g, 3.17 ml, 18.9 mmol), BINAP (737 mg, 1.18 mmol) and $Pd_2(dba)_3$ (361 mg, 0.39 mmol) were dissolved under Argon in dry and de-aerated toluene (108 ml) and treated with sodium tert-butoxide (2.12 g, 22.1 mmol). The dark brown mixture was stirred at 90° C. for 18 h. The yellow/brown reaction mixture was diluted with toluene (100 ml), cooled to rt and extracted twice with water. The organic layer was separated, dried over magnesium sulfate and concentrated in vacuo. The crude product was diluted with 50 ml hexane, stirred for 1 h and filtered off, leading to a yellow solid (7.4 g) which was purified by column chromatography (50 g silicagel, 5% to 15% ethylacetate/heptane). The combined and concentrated fractions were suspended in hexane, stirred for 17 h, filtered off andf dried in high vacuo, to yield 6.15 g (86%) yellow solid. MS (ISP): 443.4 ([M+H]$^+$).

Step d) (R)-tert-butyl 2-(4-aminophenyl)morpholine-4-carboxylate

A suspension of (R)-tert-butyl 2-(4-(diphenylmethylene-amino)phenyl)morpholine-4-carboxylate (6 g, 13.6 mmol), ammonium formate (12.8 g, 203 mmol) and Pd/$C_5$% (721 mg, 0.339 mmol) in methanol (103 ml) was stirred at 60° C. for 2 h. The reaction mixture was filtered and concentrated. The residue was dissolved in ethyl acetate and water. The organic phase was extracted twice with 0.5M HCl. The combined aqueous phases were basified with 2M-NaOH and extracted twice with DCM. The organic phases were dried over magnesium sulfate, filtered and dried in vacuo, to yield 3.04 g off-white solid. MS (ISP): 279.1 ([M+H]$^+$).

Example 13

(R)-3-(2-chlorophenyl)-N-(4-(morpholin-2-yl)phenyl)-1H-pyrazole-5-carboxamide hydrochloride

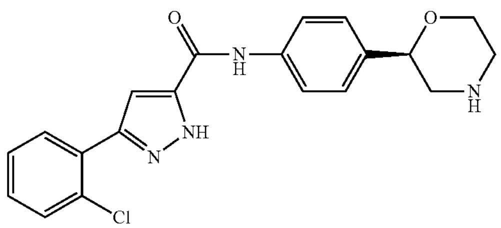 [SMILES: O=C(Nc1ccc([C@@H]2CNCCO2)cc1)c1cc(-c2ccccc2Cl)n[nH]1]

The title compound was prepared in analogy to Example 1 using (R)-tert-butyl 2-(4-aminophenyl)morpholine-4-carboxylate (prepared in Example 12) instead of (S)-tert-butyl 2-(4-aminophenyl)morpholine-4-carboxylate and 3-(2-chlorophenyl)-1H-pyrazole-5-carboxylic acid (CAS-890621-13-3) instead of 3-phenyl-1H-pyrazole-5-carboxylic acid. Light brown solid. MS (ISP): 383.1 ([M+H]$^+$).

Example 14

(S)-3-(4-chlorophenyl)-N-(4-(morpholin-2-yl)phenyl)-1H-pyrazole-5-carboxamide hydrochloride

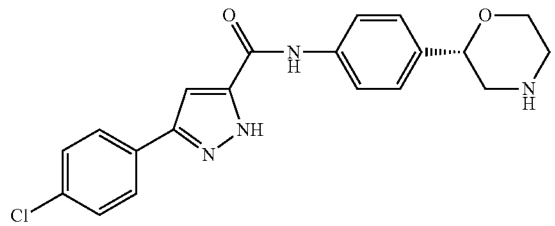 [SMILES: O=C(Nc1ccc([C@H]2CNCCO2)cc1)c1cc(-c2ccc(Cl)cc2)n[nH]1]

The title compound was prepared in analogy to Example 1 using 3-(4-chlorophenyl)-1H-pyrazole-5-carboxylic acid (CAS-54006-63-2) instead of 3-phenyl-1H-pyrazole-5-carboxylic acid. Off-white solid. MS (ISP): 383.1 ([M+H]$^+$).

Example 15

(R)-3-(3-chlorophenyl)-N-(4-(morpholin-2-yl)phenyl)-1H-pyrazole-5-carboxamide hydrochloride

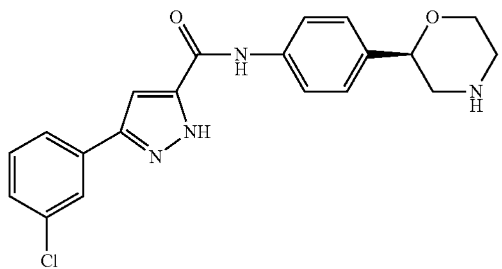 [SMILES: O=C(Nc1ccc([C@@H]2CNCCO2)cc1)c1cc(-c2cccc(Cl)c2)n[nH]1]

The title compound was prepared in analogy to Example 1 using (R)-tert-butyl 2-(4-aminophenyl)morpholine-4-carboxylate (prepared in Example 12) instead of (S)-tert-butyl 2-(4-aminophenyl)morpholine-4-carboxylate and 3-(3-chlorophenyl)-1H-pyrazole-5-carboxylic acid (CAS-595610-50-7) instead of 3-phenyl-1H-pyrazole-5-carboxylic acid. White solid. MS (ISP): 383.1 ([M+H]$^+$).

Example 16

(R)-3-(3-methoxyphenyl)-N-(4-(morpholin-2-yl)phenyl)-1H-pyrazole-5-carboxamide hydrochloride

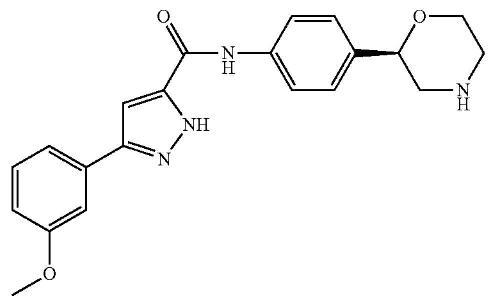 [SMILES: COc1cccc(-c2cc(C(=O)Nc3ccc([C@@H]4CNCCO4)cc3)[nH]n2)c1]

The title compound was prepared in analogy to Example 1 using (R)-tert-butyl 2-(4-aminophenyl)morpholine-4-carboxylate (prepared in Example 12) instead of (S)-tert-butyl 2-(4-aminophenyl)morpholine-4-carboxylate and 3-(3-methoxyphenyl)-1H-pyrazole-5-carboxylic acid (CAS-890591-64-7) instead of 3-phenyl-1H-pyrazole-5-carboxylic acid. White solid. MS (ISP): 379.2 ([M+H]$^+$).

Example 17

(S)-3-(3-chlorophenyl)-1-methyl-N-(4-(morpholin-2-yl)phenyl)-1H-pyrazole-5-carboxamide hydrochloride

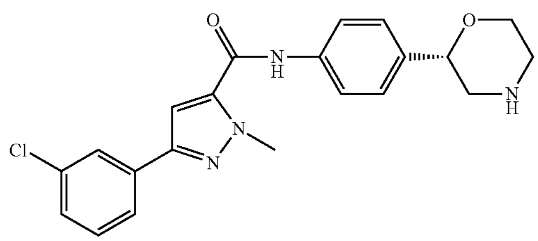 [SMILES: Cn1nc(-c2cccc(Cl)c2)cc1C(=O)Nc1ccc([C@H]2CNCCO2)cc1]

The title compound was prepared in analogy to Example 1 using 5-(3-Chloro-phenyl)-2-methyl-2H-pyrazole-3-carboxylic acid (CAS-93618-32-7) instead of 3-phenyl-1H-pyrazole-5-carboxylic acid. White solid. MS (ISP): 397.1 ([M+H]$^+$).

Example 18

(S)-1-methyl-N-(4-(morpholin-2-yl)phenyl)-5-phenyl-1H-pyrazole-3-carboxamide hydrochloride

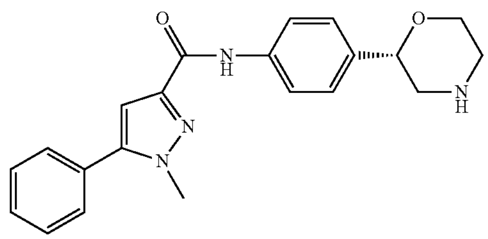 [SMILES: Cn1nc(C(=O)Nc2ccc([C@H]3CNCCO3)cc2)cc1-c1ccccc1]

The title compound was prepared in analogy to Example 1 using 1-Methyl-5-phenyl-1H-pyrazole-3-carboxylic acid (CAS-10199-53-8) instead of 3-phenyl-1H-pyrazole-5-carboxylic acid. Off-white solid. MS (ISP): 363.2 ([M+H]$^+$).

Example 19

(R)-1-methyl-N-(4-(morpholin-2-yl)phenyl)-3-phenyl-1H-pyrazole-5-carboxamide hydrochloride

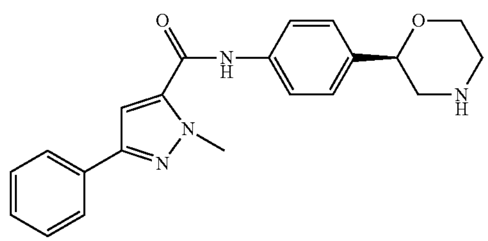 [SMILES: Cn1nc(-c2ccccc2)cc1C(=O)Nc1ccc([C@@H]2CNCCO2)cc1]

The title compound was prepared in analogy to Example 1 using (R)-tert-butyl 2-(4-aminophenyl)morpholine-4-carboxylate (prepared in Example 12) instead of (S)-tert-butyl 2-(4-aminophenyl)morpholine-4-carboxylate and 1-Methyl-3-phenyl-1H-pyrazole-5-carboxylic acid (CAS-10250-64-3) instead of 3-phenyl-1H-pyrazole-5-carboxylic acid. White solid. MS (ISP): 363.3 ([M+H]$^+$).

Example 20

(S)-5-(3-cyanophenyl)-N-(4-(morpholin-2-yl)phenyl)-1H-pyrazole-3-carboxamide hydrochloride

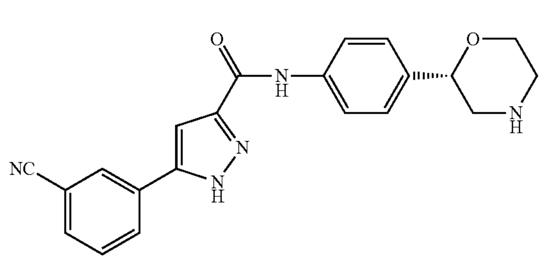 [SMILES: N#Cc1cccc(-c2cc(C(=O)Nc3ccc([C@H]4CNCCO4)cc3)n[nH]2)c1]

The title compound was prepared in analogy to Example 1 using 5-(3-Cyano-phenyl)-1H-pyrazole-3-carboxylic acid (CAS-1242427-10-6) instead of 3-phenyl-1H-pyrazole-5-carboxylic acid. Light brown solid. MS (ISP): 374.0 ([M+H]$^+$).

Example 21

(S)-3-(4-cyanophenyl)-1-methyl-N-(4-(morpholin-2-yl)phenyl)-1H-pyrazole-5-carboxamide hydrochloride

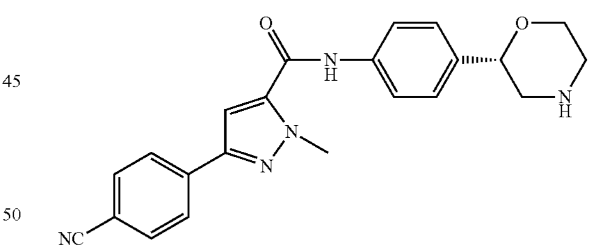

The title compound was prepared in analogy to Example 1 using 3-(4-cyanophenyl)-1-methyl-1H-pyrazole-5-carboxylic acid instead of 3-phenyl-1H-pyrazole-5-carboxylic acid. Light brown solid. MS (ISP): 388.0 ([M+H]$^+$).

Preparation of 3-(4-cyanophenyl)-1-methyl-1H-pyrazole-5-carboxylic acid

Step a) (Z)-ethyl 4-(4-cyanophenyl)-2-hydroxy-4-oxobut-2-enoate

In a dry flask, under argon atmosphere, sodium (317 mg, 13.8 mmol, Eq: 1.00) was added portionwise to ethanol (9.0 ml). (The temperature increased to 60° C.). The reaction mixture was cooled at 0° C. Then Diethyl oxalate (2.01 g, 1.87 ml, 13.8 mmol, Eq: 1.00) was added dropwise followed by 4-acetylbenzonitrile (2 g, 13.8 mmol, Eq: 1.00) in Ethanol (3.00 ml). A white solid appeared. The reaction was stirred with mechanical stirrer overnight and monitored by TLC. Then the reaction mixture was concentrated in vacuo. The residue was cooled at 0° C. and water was added to the flask. 1M HCl was added to this solution (pH=3), then the solution was extracted two times with EtOAc. The organic layer was washed three times with 20 mL Brine. The resulting organic layer was dried over MgSO4, filtered and concentrated in vacuo to give an off-white solid. This off-white solid was mixed with Ether at 0° C. The suspension was filtered to give a white solid (2.082 g, 61.6%).

Step b) Ethyl 3-(4-cyanophenyl)-1-methyl-1H-pyrazole-5-carboxylate

Under argon atmosphere (Z)-ethyl 4-(4-cyanophenyl)-2-hydroxy-4-oxobut-2-enoate (500 mg, 2.04 mmol, Eq: 1.00) was dissolved in Ethanol (10 ml) at rt. Methylhydrazine (95.9 mg, 110 μl, 2.04 mmol, Eq: 1.00) was added dropwise (The solution became yellow). The solution was stirred overnight at rt followed by 6 h heating at 50° C., cooled down to rt and concentrated. in vacuo. The residue was directly purified by column chromatography (20 g) Heptane/EtOAC:9/1 to give the expected pyrazole (173 mg, 33.2%) as a white solid. MS (ISP): 256.3 ([M+H]$^+$).

Step c) 3-(4-cyanophenyl)-1-methyl-1H-pyrazole-5-carboxylic acid

To a solution of ethyl 3-(4-cyanophenyl)-1-methyl-1H-pyrazole-5-carboxylate (70 mg, 274 μmol, Eq: 1.00) in THF (5 ml) and MeOH (1.00 ml) was added LiOH 1M (548 μl, 548 μmol, Eq: 2). The mixture was stirred for ca. 8 h at rt., then treated with water and HCl 1N (pH:3). The mixture was extracted two times with ethyl acetate. The resulting organic layers were combined, washed with Brine and dried over MgSO4, filtered and concentrated to give the desired compound (55 mg, 88.3%) as a white solid.

MS (ISP): 228.2 (M+1).

Example 22

(S)-3-(4-fluorophenyl)-1-methyl-N-(4-(morpholin-2-yl)phenyl)-1H-pyrazole-5-carboxamide hydrochloride

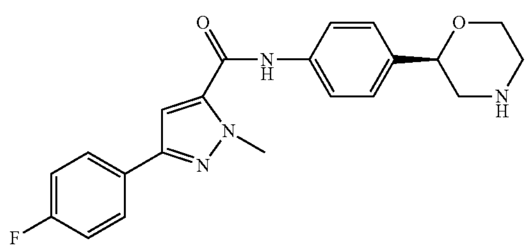 [SMILES: Cn1nc(-c2ccc(F)cc2)cc1C(=O)Nc1ccc([C@@H]2CNCCO2)cc1]

The title compound was prepared in analogy to Example 1 using 5-(4-Fluoro-phenyl)-2-methyl-1H-pyrazole-3-carboxylic acid (CAS-943863-70-5) instead of 3-phenyl-1H-pyrazole-5-carboxylic acid. Light brown solid. MS (ISP): 381.1 ([M+H]$^+$).

Example 23

(S)-3-(3-methoxyphenyl)-1-methyl-N-(4-(morpholin-2-yl)phenyl)-1H-pyrazole-5-carboxamide hydrochloride

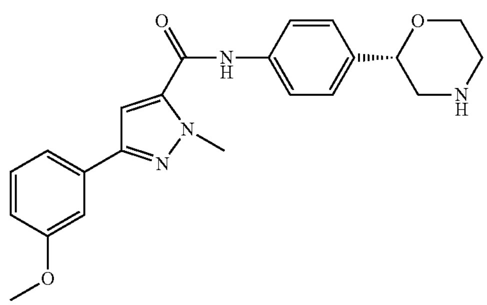 [SMILES: COc1cccc(-c2cc(C(=O)Nc3ccc([C@H]4CNCCO4)cc3)n(C)n2)c1]

The title compound was prepared in analogy to Example 1 using 5-(3-Methoxy-phenyl)-2-methyl-1H-pyrazole-3-carboxylic acid (CAS-1022575-47-8) instead of 3-phenyl-1H-pyrazole-5-carboxylic acid. Light brown solid. MS (ISP): 381.1 ([M+H]$^+$).

Example 24

(S)-3-(3-cyanophenyl)-1-methyl-N-(4-(morpholin-2-yl)phenyl)-1H-pyrazole-5-carboxamide hydrochloride

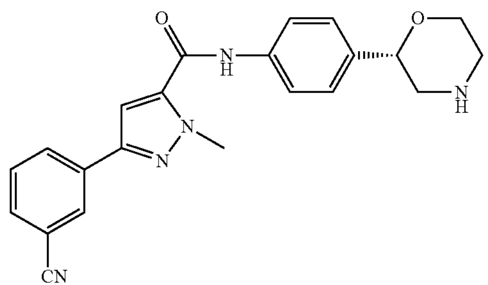 [SMILES: Cn1nc(-c2cccc(C#N)c2)cc1C(=O)Nc1ccc([C@H]2CNCCO2)cc1]

The title compound was prepared in analogy to Example 1 using 3-(3-cyanophenyl)-1-methyl-1H-pyrazole-5-carboxylic acid instead of 3-phenyl-1H-pyrazole-5-carboxylic acid. Light brown solid. MS (ISP): 388.0 ([M+H]$^+$).

Preparation of 3-(3-cyanophenyl)-1-methyl-1H-pyrazole-5-carboxylic acid

In analogy to 3-(4-cyanophenyl)-1-methyl-1H-pyrazole-5-carboxylic acid, described in Example 21.

Example 25

(S)-3-(3-cyanophenyl)-1-ethyl-N-(4-(morpholin-2-yl)phenyl)-1H-pyrazole-5-carboxamide hydrochloride

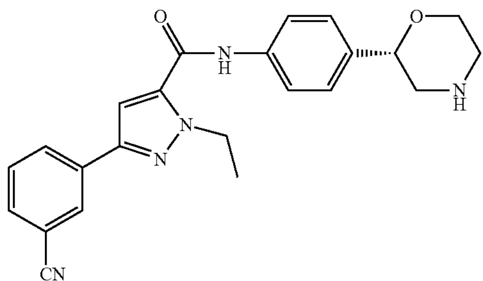 [SMILES: CCn1nc(-c2cccc(C#N)c2)cc1C(=O)Nc1ccc([C@H]2CNCCO2)cc1]

The title compound was prepared in analogy to Example 1 using 3-(3-cyanophenyl)-1-ethyl-1H-pyrazole-5-carboxylic acid instead of 3-phenyl-1H-pyrazole-5-carboxylic acid. Off-white solid. MS (ISP): 402.1 ([M+H]$^+$).

Preparation of 3-(3-cyanophenyl)-1-ethyl-1H-pyrazole-5-carboxylic acid

In analogy to 3-(4-cyanophenyl)-1-methyl-1H-pyrazole-5-carboxylic acid, described in Example 21.

Example 26

(S)-3-(4-cyanophenyl)-1-ethyl-N-(4-(morpholin-2-yl)phenyl)-1H-pyrazole-5-carboxamide hydrochloride

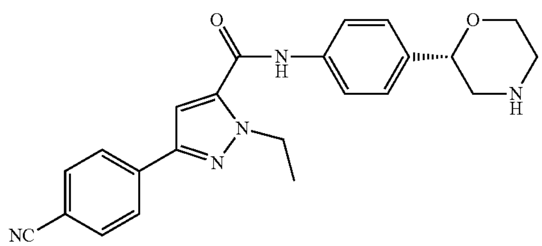 [SMILES: CCn1nc(-c2ccc(C#N)cc2)cc1C(=O)Nc1ccc([C@H]2CNCCO2)cc1]

The title compound was prepared in analogy to Example 1 using 3-(4-cyanophenyl)-1-ethyl-1H-pyrazole-5-carboxylic acid instead of 3-phenyl-1H-pyrazole-5-carboxylic acid. Off-white solid. MS (ISP): 402.1 ([M+H]$^+$).

Preparation of 3-(4-cyanophenyl)-1-ethyl-1H-pyrazole-5-carboxylic acid

In analogy to 3-(4-cyanophenyl)-1-methyl-1H-pyrazole-5-carboxylic acid, described in Example 21.

Example 27

(S)-5-(3-cyanophenyl)-4-methyl-N-(4-(morpholin-2-yl)phenyl)-1H-pyrazole-3-carboxamide hydrochloride

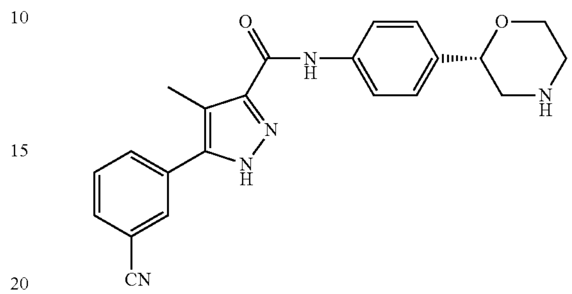

The title compound was prepared in analogy to Example 1 using 5-(3-cyanophenyl)-4-methyl-1H-pyrazole-3-carboxylic acid instead of 3-phenyl-1H-pyrazole-5-carboxylic acid. Brown solid. MS (ISP): 388.1 ([M+H]$^+$).

Preparation of 5-(3-cyanophenyl)-4-methyl-1H-pyrazole-3-carboxylic acid

Step a) lithium (Z)-4-(3-cyanophenyl)-1-ethoxy-3-methyl-1,4-dioxobut-2-en-2-olate To a magnetically stirred solution of LiHMDS in THF 1M (7.94 ml, 7.94 mmol, Eq: 1.00) in Et2O (50 ml) at −78° C. was added dropwise a solution of 3-propionylbenzonitrile (1.264 g, 7.94 mmol, Eq: 1.00) in Et2O (10.0 ml) under argon atmosphere. After the mixture was stirred at the same temperature for an additional period of 45 min, diethyl oxalate (1.22 g, 1.13 ml, 8.34 mmol, Eq: 1.05) was added dropwise. The reaction mixture was allowed to warm to rt and stirred for 3 days. The precipitate formed was collected by filtration, washed with diethyl ether, and dried under vacuum to afford the desired lithium salt as a yellow solid (929 mg, 44.1%).

Step b) Ethyl 5-(3-cyanophenyl)-4-methyl-1H-pyrazole-3-carboxylate

To a solution of lithium (Z)-4-(3-cyanophenyl)-1-ethoxy-3-methyl-1,4-dioxobut-2-en-2-olate (400 mg, 1.51 mmol, Eq: 1.00) in Ethanol (10 ml) was added Hydrazine hydrochloride (113 mg, 1.65 mmol, Eq: 1.093) at rt to give an orange solution. The resulting mixture was stirred overnight at the same temperature. After 1 day the solvent was removed under reduce pressure and to the mixture was added brine. The solution was extracted two times with AcOEt, and the combined organic layers were dried over $MgSO_4$, filtered and concentrated to give the desired compound as a yellow gum (114 mg, 26.6%). MS (ISP): 256.0 ([M+H]$^+$).

Step c) 3-(3-cyanophenyl)-1-methyl-1H-pyrazole-5-carboxylic acid

To a solution of ethyl 5-(3-cyanophenyl)-4-methyl-1H-pyrazole-3-carboxylate (100 mg, 392 μmol, Eq: 1.00) in THF (5 ml) in MeOH (1.00 ml) was added LiOH 1M (2.35 ml, 2.35 mmol, Eq: 6). The mixture was stirred overnight. To the residue was added water and HCl 1N (pH:1), this aqueous phase was extracted two times with ethyl acetate, the resulting organic layers were combined and washed with brine, dried over MgSO4, filtered and concentrated in vacuo to afford the desired compound (52 mg, 52.6%) as a yellow solid. MS (ISP): 228.1 (M+1).

Example 28

(S)-5-(5-cyano-2-fluorophenyl)-N-(4-(morpholin-2-yl)phenyl)-1H-pyrazole-3-carboxamide hydrochloride

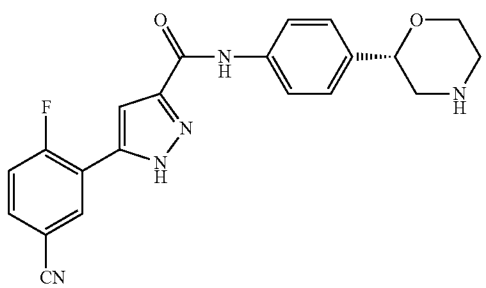 [SMILES: N#Cc1ccc(F)c(-c2cc(C(=O)Nc3ccc([C@H]4CNCCO4)cc3)n[nH]2)c1]

The title compound was prepared in analogy to Example 1 using 5-(5-cyano-2-fluorophenyl)-1H-pyrazole-3-carboxylic acid instead of 3-phenyl-1H-pyrazole-5-carboxylic acid. Brown solid. MS (ISP): 392.0 ([M+H]$^+$).

Preparation of 5-(5-cyano-2-fluorophenyl)-1H-pyrazole-3-carboxylic acid

In analogy to 5-(3-cyanophenyl)-4-methyl-1H-pyrazole-3-carboxylic acid, described in Example 21.

Example 29

(S)-1-(4-Fluorophenyl)-N-(4-(morpholin-2-yl)phenyl)-1H-pyrazole-3-carboxamide hydrochloride

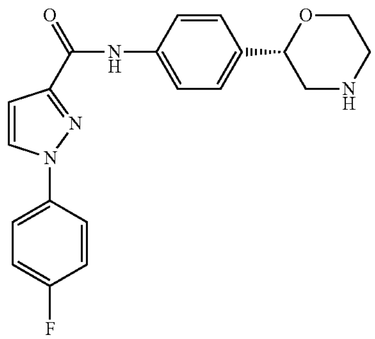 [SMILES: O=C(Nc1ccc([C@H]2CNCCO2)cc1)c1ccn(-c2ccc(F)cc2)n1]

The title compound was prepared in analogy to Example 1 using 1-(4-fluorophenyl)-1H-pyrazole-3-carboxylic acid (CAS-1152535-34-6) in THF instead of 3-phenyl-1H-pyrazole-5-carboxylic acid in DMF. White solid. MS (ISP): 367.0 ([M+H]$^+$).

Example 30

(S)—N-(4-(Morpholin-2-yl)phenyl)-1-phenyl-1H-pyrazole-5-carboxamide hydrochloride

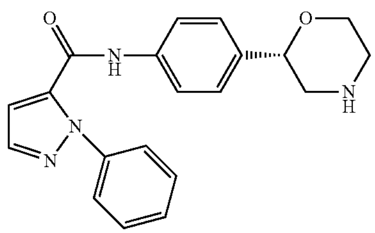 [SMILES: O=C(Nc1ccc([C@H]2CNCCO2)cc1)c1ccnn1-c1ccccc1]

The title compound was prepared in analogy to Example 1 using 1-phenyl-1H-pyrazole-5-carboxylic acid (CAS-1133-77-3) instead of 3-phenyl-1H-pyrazole-5-carboxylic acid. White solid. MS (ISP): 349.1 ([M+H]$^+$).

Example 31

(R)-1-(4-Fluorophenyl)-N-(4-(morpholin-2-yl)phenyl)-1H-pyrazole-3-carboxamide hydrochloride

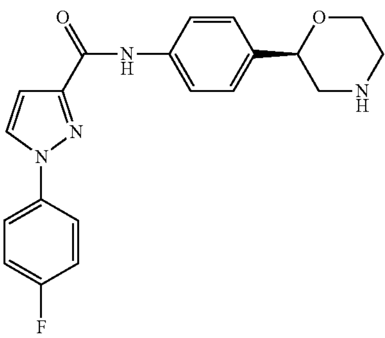 [SMILES: O=C(Nc1ccc([C@@H]2CNCCO2)cc1)c1ccn(-c2ccc(F)cc2)n1]

The title compound was prepared in analogy to Example 1 using (R)-tert-butyl 2-(4-aminophenyl)morpholine-4-carboxylate instead of (S)-tert-butyl 2-(4-aminophenyl)morpholine-4-carboxylate and 1-(4-fluorophenyl)-1H-pyrazole-3-carboxylic acid (CAS-1152535-34-6) instead of 3-phenyl-1H-pyrazole-5-carboxylic acid. White solid. MS (ISP): 367.0 ([M+H]$^+$).

Example 32

(S)-1-(5-Chloropyridin-2-yl)-N-(4-(morpholin-2-yl)phenyl)-1H-pyrazole-3-carboxamide hydrochloride

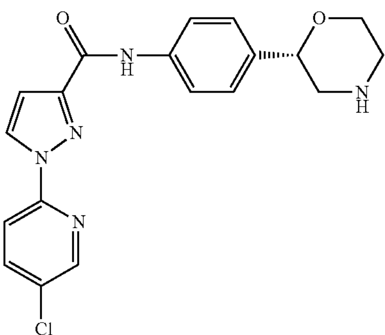 [SMILES: O=C(Nc1ccc([C@H]2CNCCO2)cc1)c1ccn(-c2ccc(Cl)cn2)n1]

The title compound was obtained in analogy to example 47 using 2-bromo-5-chloropyridine instead of 2-chloro-5-(trifluoromethyl)pyrimidine in step b). Off-white solid. MS (ISP): 384.2 ([M+H]$^+$).

Example 33

(S)—N-(4-(Morpholin-2-yl)phenyl)-1-(5-(trifluoromethyl)pyridin-2-yl)-1H-pyrazole-3-carboxamide hydrochloride

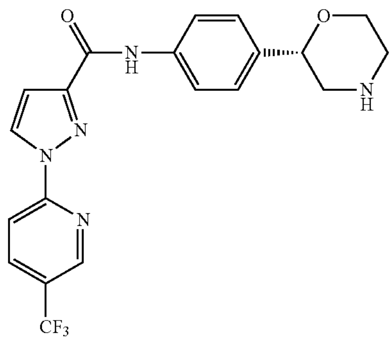 [SMILES: O=C(Nc1ccc([C@H]2CNCCO2)cc1)c1ccn(-c2ccc(C(F)(F)F)cn2)n1]

The title compound was obtained in analogy to example 47 using 2-bromo-5-(trifluoromethyl)pyridine instead of 2-chloro-5-(trifluoromethyl)pyrimidine in step b). White solid. MS (ISP): 418.2 ([M+H]$^+$).

Example 34

(S)-1-(4-Cyanophenyl)-N-(4-(morpholin-2-yl)phenyl)-1H-pyrazole-3-carboxamide hydrochloride

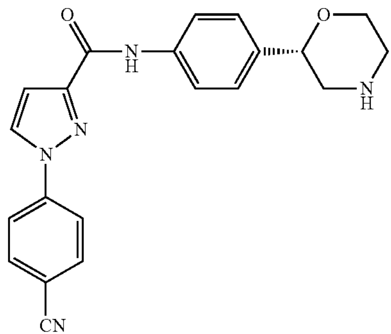 [SMILES: N#Cc1ccc(-n2ccc(C(=O)Nc3ccc([C@H]4CNCCO4)cc3)n2)cc1]

The title compound was obtained in analogy to example 47 using 2-bromo-benzonitrile instead of 2-chloro-5-(trifluoromethyl)pyrimidine in step b). Off-white solid. MS (ISP): 374.3 ([M+H]$^+$).

Example 35

(R)—N-(4-(Morpholin-2-yl)phenyl)-1-(5-(trifluoromethyl)pyridin-2-yl)-1H-pyrazole-3-carboxamide hydrochloride

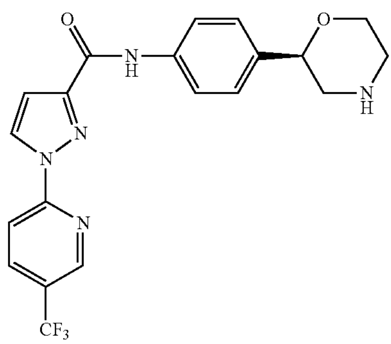 [SMILES: O=C(Nc1ccc([C@@H]2CNCCO2)cc1)c1ccn(-c2ccc(C(F)(F)F)cn2)n1]

The title compound was prepared in analogy to Example 1 using (R)-tert-butyl 2-(4-aminophenyl)morpholine-4-carboxylate instead of (S)-tert-butyl 2-(4-aminophenyl)morpholine-4-carboxylate and 1-(5-Trifluoromethyl-pyridin-2-yl)-1H-pyrazole-3-carboxylic acid (CAS-1006962-72-6) instead of 3-phenyl-1H-pyrazole-5-carboxylic acid. White solid. MS (ISP): 418.2 ([M+H]$^+$).

Example 36

(S)-3-(3-Cyanophenyl)-N-(4-(piperidin-3-yl)phenyl)-1H-pyrazole-5-carboxamide hydrochloride

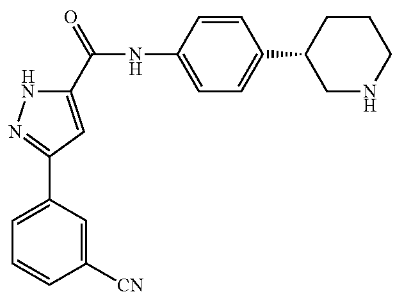 [SMILES: N#Cc1cccc(-c2cc(C(=O)Nc3ccc([C@@H]4CCCNC4)cc3)[nH]n2)c1]

The title compound was prepared in analogy to Example 1 using 5-(3-Cyano-phenyl)-1H-pyrazole-3-carboxylic acid (CAS-1242427-10-6) instead of 3-phenyl-1H-pyrazole-5-carboxylic acid. White solid. MS (ISP): 372.0 ([M+H]$^+$).

Example 37

(R)-3-(3-Cyanophenyl)-N-(4-(piperidin-3-yl)phenyl)-1H-pyrazole-5-carboxamide hydrochloride

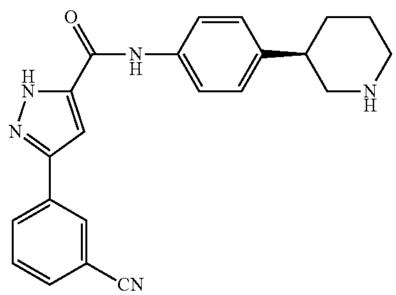 [SMILES: N#Cc1cccc(-c2cc(C(=O)Nc3ccc([C@H]4CCCNC4)cc3)[nH]n2)c1]

The title compound was prepared in analogy to Example 1 using (R)-tert-butyl 2-(4-aminophenyl)morpholine-4-carboxylate instead of (S)-tert-butyl 2-(4-aminophenyl)morpholine-4-carboxylate and 5-(3-Cyano-phenyl)-1H-pyrazole-3-carboxylic acid (CAS-1242427-10-6) instead of 3-phenyl-1H-pyrazole-5-carboxylic acid. White solid. MS (ISP): 372.0 ([M+H]$^+$).

Example 38

(rac) 3-(3-Cyanophenyl)-N-(4-(pyrrolidin-3-yl)phenyl)-1H-pyrazole-5-carboxamide hydrochloride

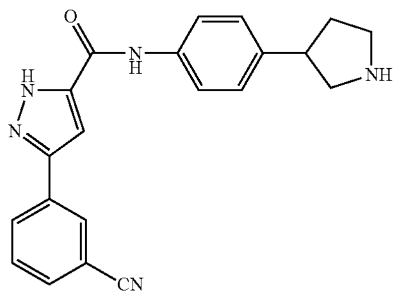 [SMILES: N#Cc1cccc(-c2cc(C(=O)Nc3ccc(C4CCNC4)cc3)[nH]n2)c1]

The title compound was prepared in analogy to Example 1 using 3-(4-Amino-phenyl)-pyrrolidine-1-carboxylic acid tert-butyl ester (CAS-908334-28-1) instead of (S)-tert-butyl 2-(4-aminophenyl)morpholine-4-carboxylate and 5-(3-Cyano-phenyl)-1H-pyrazole-3-carboxylic acid (CAS-1242427-10-6) instead of 3-phenyl-1H-pyrazole-5-carboxylic acid. White solid. MS (ISP): 357.8 ($[M+H]^+$).

Example 39

(S)-5-(3-Cyano-4-fluorophenyl)-N-(4-(morpholin-2-yl)phenyl)-1H-pyrazole-3-carboxamide hydrochloride

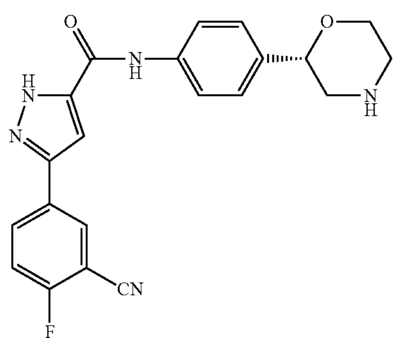 [SMILES: N#Cc1cc(-c2cc(C(=O)Nc3ccc([C@H]4CNCCO4)cc3)[nH]n2)ccc1F]

The title compound was prepared in analogy to Example 1 using 5-(3-Cyano-4-fluoro-phenyl)-1H-pyrazole-3-carboxylic acid (prepared as indicated below: a-d) instead of 3-phenyl-1H-pyrazole-5-carboxylic acid. White solid. MS (ISP): 392.1 ($[M+H]^+$).

Preparation of 5-(3-Cyano-4-fluoro-phenyl)-1H-pyrazole-3-carboxylic acid a) Lithium (Z)-4-(3-bromo-4-fluorophenyl)-1-ethoxy-1,4-dioxobut-2-en-2-olate: to a magnetically stirred solution of LiHMDS in THF 1M (9.22 ml, 9.22 mmol, Eq: 1) was added Et2O (31.2 ml) at −78° C. to give a yellow solution. To this mixture was added a solution of 1-(3-bromo-4-fluorophenyl) ethanone (2 g, 9.22 mmol, Eq: 1.00) in Et2O (15.6 ml) dropwise under argon atmosphere. The mixture was then stirred at the same temperature for an additional period of 45 min. Diethyl oxalate (1.41 g, 1.31 ml, 9.68 mmol, Eq: 1.05) was then added dropwise. The reaction mixture was allowed to warm to rt and stirred for another 2 days. The precipitate formed was collected by filtration, washed with diethyl ether, and dried under vacuum to afford the desired lithium salt as a light-yellow solid (2.677 g, 89.9%).

b) Ethyl 5-(3-bromo-4-fluorophenyl)-1H-pyrazole-3-carboxylate: To a solution of lithium (Z)-4-(3-bromo-4-fluorophenyl)-1-ethoxy-1,4-dioxobut-2-en-2-olate (600 mg, 1.86 mmol, Eq: 1.00) in Ethanol (25 ml) was added Hydrazine monohydrate (139 mg, 2.03 mmol, Eq: 1.093) at rt to give a white suspension, after 1 h the suspension became a solution. The resulting mixture was stirred overnight. After 1 day the reaction was complete After stirring the solvent was removed under reduce pressure and to the mixture was added brine, the solution was extracted two times with AcOEt, and the combined organic layers were dried over Na2SO4, filtered and concentrated to give ethyl 5-(3-bromo-4-fluorophenyl)-1H-pyrazole-3-carboxylate as a white solid (460 mg, 79.1%). MS (ISP): 314.8 ($[M+H]^+$).

c) Ethyl 5-(3-cyano-4-fluorophenyl)-1H-pyrazole-3-carboxylate: A mixture of ethyl 5-(3-bromo-4-fluorophenyl)-1H-pyrazole-3-carboxylate (300 mg, 958 μmol, Eq: 1.00), Zinc Cyanide (65.2 mg, 556 μmol, Eq: 0.58) and Pd(PPh3)4 (111 mg, 95.8 μmol, Eq: 0.1) was heated at 160° C. in DMF (2 ml) (stored over molecular sieves) for 30 mins in microwave. The mixture was partitioned between EtOAc (40 mL) and 2N NH4OH (40 mL). The organic phase was extracted with 2N NH4OH, washed with Brine, dried over MgSO4 and concentrated in vacuo. The crude mixture was purified by column chromatography (10 g) eluent: Heptane/EtOAc: 95/5 to give the desired nitrile compound as a white crystalline solid (180 mg, 72.5%). MS (ISP): 260.0 ($[M+H]^+$).

d) 5-(3-cyano-4-fluorophenyl)-1H-pyrazole-3-carboxylic acid: To a solution of ethyl 5-(3-cyano-4-fluorophenyl)-1H-pyrazole-3-carboxylate (180 mg, 694 μmol, Eq: 1.00) in THF (5.00 ml) and MeOH (1 ml) was added LiOH 1M (4.17 ml, 4.17 mmol, Eq: 6). The mixture was stirred overnight. After addition of LiOH the solution was become orange. To the residue was added water and HCl 1N (pH: 1), this aqueous phase was extracted two times with ethyl acetate; the resulting organic layers were combined and washed with Brine. Then dried over MgSO4, filtered and concentrated to give the desired compound (45 mg, 22.4%) as a white solid. MS (ISP): 232.4 ($[M+H]^+$).

Example 40

(S)-3-(3-(Difluoromethoxy)phenyl)-N-(4-(morpholin-2-yl)phenyl)-1H-pyrazole-5-carboxamide hydrochloride

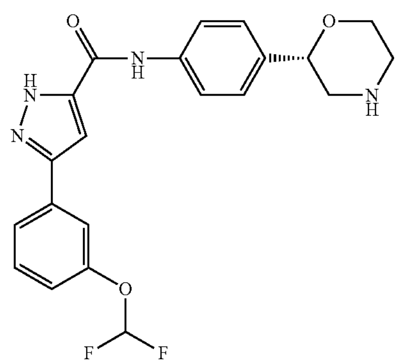 [SMILES: O=C(Nc1ccc([C@H]2CNCCO2)cc1)c1cc(-c2cccc(OC(F)F)c2)n[nH]1]

The title compound was prepared in analogy to Example 1 using 5-(3-Difluoromethoxy-phenyl)-2H-pyrazole-3-carboxylic acid (prepared as indicated below: a-c) instead of 3-phenyl-1H-pyrazole-5-carboxylic acid. White solid. MS (ISP): 415.2 ($[M+H]^+$).

Preparation of 5-(3-Difluoromethoxy-phenyl)-2H-pyrazole-3-carboxylic acid a) 5-(3-Difluoromethoxy-phenyl)-2H-pyrazole-3-carboxylic acid methyl ester: To a solution of (Z)-methyl 4-(3-(difluoromethoxy)phenyl)-2-hydroxy-4-oxobut-2-enoate (CAS-832741-03-4) (800 mg, 2.94 mmol, Eq: 1.00) in Ethanol (20 ml) was added Hydrazine hydrochloride (220 mg, 3.21 mmol, Eq: 1.093) at rt to give an orange suspension. The resulting mixture was stirred overnight at the same temperature. After 1 day the reaction was complete. After stirring the solvent was removed under reduce pressure and to the mixture was added brine, the solution was extracted two times with AcOEt, and the combined organic layers were dried over $MgSO_4$, filtered and concentrated to give the desired compound as a light-brown solid (630 mg, 79.9%). MS (ISP): 269.0 ($[M+H]^+$).

b) 5-(3-Difluoromethoxy-phenyl)-2H-pyrazole-3-carboxylic acid: To a solution of 5-(3-Difluoromethoxy-phenyl)-2H-pyrazole-3-carboxylic acid methyl ester (620 mg, 2.31 mmol, Eq: 1.00) in THF (10 ml) and MeOH (2.00 ml) was added LiOH 1M (13.9 ml, 13.9 mmol, Eq: 6) to give a brown solution. The mixture was stirred overnight. After addition of LiOH the solution was become. To the residue was added water and HCl 1N (pH:1), this aqueous phase was extracted two times with ethyl acetate, the resulting organic layers were combined and washed with Brine. Then dried over MgSO4, filtered and concentrated to give the desired compound (510 mg, 86.8%) as a light-yellow solid. MS (ISP): 255.0 ($[M+H]^+$).

Example 41

(S)-5-(3-(Difluoromethoxy)phenyl)-1-ethyl-N-(4-(morpholin-2-yl)phenyl)-1H-pyrazole-3-carboxamide hydrochloride

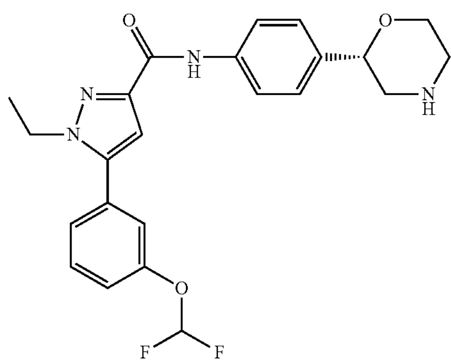 [SMILES: CCn1nc(C(=O)Nc2ccc([C@H]3CNCCO3)cc2)cc1-c1cccc(OC(F)F)c1]

a) (S)-Tert-butyl 2-(4-(3-(3-(difluoromethoxy)phenyl)-1H-pyrazole-5-carboxamido)phenyl)morpholine-4-carboxylate: In a 25 mL round-bottomed flask, 3-(3-(difluoromethoxy)phenyl)-1H-pyrazole-5-carboxylic acid (515 mg, 2.03 mmol, Eq: 1.1) (preparation described in example 40), (5)-tert-butyl 2-(4-aminophenyl)morpholine-4-carboxylate (513 mg, 1.84 mmol, Eq: 1.00) (preparation described in example 1), N-Methylmorpholine (559 mg, 608 μl, 5.53 mmol, Eq: 3) and HBTU (1.05 g, 2.76 mmol, Eq: 1.5) were combined with DMF (2 ml) to give a yellow solution. The reaction mixture was stirred overnight at 60° C. The mixture was poured into water (10 ml) and extracted twice with EtOAc. The organic layers were washed with NaHCO3, brine, dried over MgSO4, filtered and concentrated in vacuo to give a brown crude mixture. This mixture was diluted with Heptane, stirred for 15 minutes and the suspension was filtered. The resulting solid was washed several times with Heptane to afford the desired compound as a brown solid (550 mg, 58.0%).

b) (S)-Tert-butyl 2-(4-(5-(3-(difluoromethoxy)phenyl)-1-ethyl-1H-pyrazole-3-carboxamido)phenyl)morpholine-4-carboxylate and (S)-tert-butyl 2-(4-(3-(3-(difluoromethoxy)phenyl)-1-ethyl-1H-pyrazole-5-carboxamido)phenyl)morpholine-4-carboxylate:

c) To a mixture of (S)-tert-butyl 2-(4-(3-(3-(difluoromethoxy)phenyl)-1H-pyrazole-5-carboxamido)phenyl)morpholine-4-carboxylate (70 mg, 136 μmol, Eq: 1.00) and potassium carbonate (41.4 mg, 299 μmol, Eq: 2.2) in DMF (2 ml) was added iodoethane (25.5 mg, 13.2 μl, 163 μmol, Eq: 1.2) and stirred overnight at rt. To the resulting mixture was added water and the organic phase was extracted with Water and Brine, then the organic layer was dried over MgSO4, filtered off and concentrated in vacuo to give the crude compound as a mixture of isomers which were separated by column chromatography (10 g-cartridge) to give: (S)-tert-butyl 2-(4-(5-(3-(difluoromethoxy)phenyl)-1-ethyl-1H-pyrazole-3-carboxamido)phenyl)morpholine-4-carboxylate (17 mg, 23.0%) and (S)-tert-butyl 2-(4-(3-(3-(difluoromethoxy)phenyl)-1-ethyl-1H-pyrazole-5-carboxamido)phenyl)morpholine-4-carboxylate (27 mg, 36.6%).

d) (S)-5-(3-(Difluoromethoxy)phenyl)-1-ethyl-N-(4-(morpholin-2-yl)phenyl)-1H-pyrazole-3-carboxamide hydrochloride: To a solution of (S)-tert-butyl 2-(4-(5-(3-(difluoromethoxy)phenyl)-1-ethyl-1H-pyrazole-3-carboxamido)phenyl)morpholine-4-carboxylate (17 mg) in Dioxane (40.8 μl) was added 4M-HCl in dioxane (117 μl, 470 μmol, Eq: 15). The reaction mixture was stirred at 60° C. overnight. To the mixture was added 2 ml of diethyl ether and stirred for 15 min at room temp. The mixture was filtered and concentrated in high vacuum to give the expected hydrochloride as a white solid (9 mg, 60.0%). MS (ISP): 443.1 ($[M+H]^+$).

Example 42

(S)-3-(3-(Difluoromethoxy)phenyl)-1-ethyl-N-(4-(morpholin-2-yl)phenyl)-1H-pyrazole-5-carboxamide hydrochloride

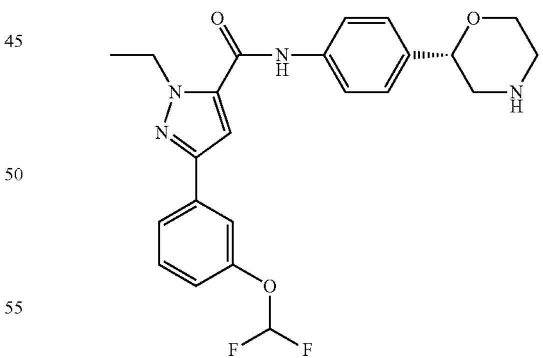

To a solution of (S)-tert-butyl 2-(4-(3-(3-(difluoromethoxy)phenyl)-1-ethyl-1H-pyrazole-5-carboxamido)phenyl)morpholine-4-carboxylate (27 mg) (prepared in Example 41, b)) in Dioxane (40.8 μl) was added 4M−HCl in dioxane (117 μl, 470 μmol, Eq: 15). The reaction mixture was stirred at 60° C. overnight. To the mixture was added 2 ml of diethyl ether and stirred for 15 min at room temp. The mixture was filtered and concentrated in high vacuum to give the expected hydrochloride as a white solid (15 mg, 63%). MS (ISP): 443.1 ($[M+H]^+$).

Example 43

(S)-3-(3-Cyano-2-fluorophenyl)-N-(4-(morpholin-2-yl)phenyl)-1H-pyrazole-5-carboxamide hydrochloride

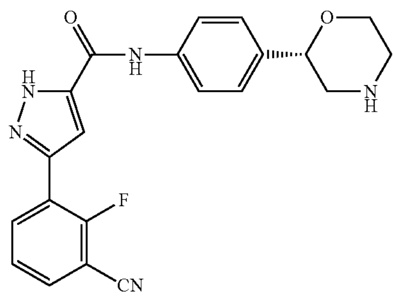 [SMILES: N#Cc1cccc(-c2cc(C(=O)Nc3ccc([C@H]4CNCCO4)cc3)[nH]n2)c1F]

The title compound was prepared in analogy to Example 39 using 1-(3-bromo-2-fluorophenyl)ethanone instead of 1-(3-bromo-4-fluorophenyl)ethanone. White solid. MS (ISP): 392.1 ([M+H]$^+$).

Example 44

(S)-3-(3-(Difluoromethoxy)phenyl)-1-methyl-N-(4-(morpholin-2-yl)phenyl)-1H-pyrazole-5-carboxamide hydrochloride

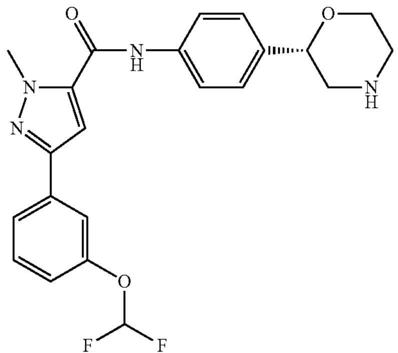 [SMILES: Cn1nc(-c2cccc(OC(F)F)c2)cc1C(=O)Nc1ccc([C@H]2CNCCO2)cc1]

The title compound was prepared in analogy to Example 42 using Methyl iodide instead of Iodoethane. White solid. MS (ISP): 429.1 ([M+H]$^+$).

Example 45

(S)-1-(4-(Difluoromethoxy)phenyl)-N-(4-(morpholin-2-yl)phenyl)-1H-pyrazole-3-carboxamide hydrochloride

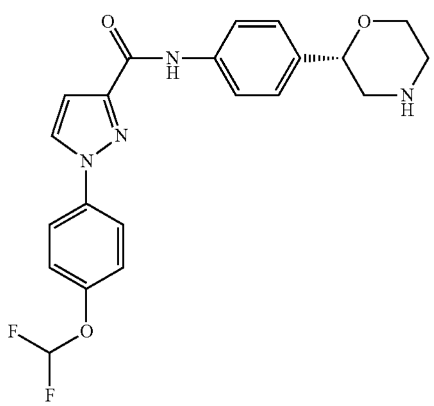 [SMILES: O=C(Nc1ccc([C@H]2CNCCO2)cc1)c1ccn(-c2ccc(OC(F)F)cc2)n1]

a) Ethyl 2-chloro-2-(2-(4-(difluoromethoxy)phenyl)hydrazono)acetate 4-(Difluoromethoxy)aniline (796 mg, 5 mmol) was dissolved in tetrafluoroboric acid (2.38 g, 1.7 ml, 13.0 mmol) and water (2 ml). After cooling to 0° C., a solution of sodium nitrite (345 mg, 5.0 mmol) in water (0.75 ml) was slowly added. The mixture was stirred for 30 min and the thick precipitate was collected by filtration and washed with diethylether (about 3 ml). The light red solid was dissolved in 1.5 ml of acetone and 5 ml of diethylether was added. After stirring for 15 min with cooling, the white solid was filtered, washed with diethylether and dried at HV for 15 min to yield 4-difluoromethoxy-benzenediazonium tetrafluoroborate.

This diazonium salt (851 mg, 3.3 mmol) was added to a solution of ethyl 2-chloro-3-oxobutanoate (494 mg, 420 μl, 3 mmol) in pyridine (0.8 ml) and water (0.8 ml). The very thick suspension was stirred at −5° C. for 30 min. The solid was filtered, washed with ice cold water and dried in vacuo to yield an orange solid (0.67 g, 76%). MS (ISP): 293.1 ([{$^{35}$Cl}M+H]$^+$), 295.2 ([{$^{37}$Cl}M+H]$^+$).

b) Ethyl 1-(4-(difluoromethoxy)phenyl)-1H-pyrazole-3-carboxylate

Ethyl 2-chloro-2-(2-(4-(difluoromethoxy)phenyl)hydrazono)acetate (585 mg, 2 mmol) was dissolved in toluene (4 ml) and 2,5-norbornadiene (906 mg, 1 ml, 9.83 mmol) and triethylamine (587 mg, 808 μl, 5.8 mmol) were added. The reaction mixture was stirred at 70° C. for 30 min and the reaction mixture was allowed to stir at room temperature overnight. The solid was filtered off and washed with toluene. The organic fraction was evaporated and the residue obtained was dissolved in xylene (12 ml) and refluxed for 2 hours. The solvent was evaporated and the residue was purified by column chromatography (50 g Silicagel, dichloromethane) to yield 387 mg (69%) of a light yellow solid. MS (ISP): 283.1 ([M+H]$^+$).

c) 1-(4-(Difluoromethoxy)phenyl)-1H-pyrazole-3-carboxylic acid

To a solution of ethyl 1-(4-(difluoromethoxy)phenyl)-1H-pyrazole-3-carboxylate (350 mg, 1.24 mmol) in a mixture of THF (3.1 ml), methanol (1.6 ml), Water (1.6 ml) lithium hydroxide hydrate (89 mg, 3.72 mmol) was added. The solution was heated to 80° C. for 2 h. Most of the organic solvent was removed under reduced pressure. Sodium bicarbonate solution and ethyl acetate were added and the organic layer was separated. The aqueous layer was made acid by addition of 25% aqueous hydrochloric acid and the mixture was extracted 2 times with ethyl acetate. The organic layers were combined, dried (MgSO4) and evaporated. The product was dried in vacuo and was directly used for the next step.

d) (S)-tert-Butyl 2-(4-(1-(4-(difluoromethoxy)phenyl)-1H-pyrazole-3-carboxamido)phenyl)morpholine-4-carboxylate (S)-tert-butyl 2-(4-aminophenyl)morpholine-4-carboxylate (110 mg, 0.39 mmol), 1-(4-(difluoromethoxy)phenyl)-1H-pyrazole-3-carboxylic acid (100 mg, 0.39 mmol), HBTU (167 mg, 0.44 mmol) and N-methylmorpholine (119 mg, 130 μl, 1.18 mmol) were combined with DMF (2 ml) to give a light yellow solution. The reaction mixture was stirred at 50° C. for 17 hours.

The reaction mixture was poured into 25 ml of water and extracted with ethyl acetate twice. The combined organic layers were washed with brine, dried over MgSO4 and concentrated in vacuo. The crude material was purified by flash chromatography (20 g Silicagel, 30 to 50% ethyl acetate in heptane) to yield an off-white solid (130 mg, 64%). MS (ISP): 459.4 (100%, $[M-tBu+H]^+$), 515.4 (5%, $[M+H]^+$).

e) (S)-1-(4-(Difluoromethoxy)phenyl)-N-(4-(morpholin-2-yl)phenyl)-1H-pyrazole-3-carboxamide hydrochloride (S)-tert-Butyl 2-(4-(1-(4-(difluoromethoxy)phenyl)-1H-pyrazole-3-carboxamido)phenyl)morpholine-4-carboxylate (130 mg, 0.25 mmol) was dissolved in dioxane (0.6 ml) and a solution of HCl in dioxane (4M, 0.12 ml, 3.8 mmol) was added. The reaction mixture was stirred overnight at 60° C. After cooling ether was added, the solid was filtered off, washed with ether and dried in vacuo to afford (S)-1-(4-(difluoromethoxy)phenyl)-N-(4-(morpholin-2-yl)phenyl)-1H-pyrazole-3-carboxamide hydrochloride (90 mg, 79%) as an off-white solid. MS (ISP): 415.4 ($[M+H]^+$).

Example 46

(R)-1-(4-(Difluoromethoxy)phenyl)-N-(4-(morpholin-2-yl)phenyl)-1H-pyrazole-3-carboxamide hydrochloride

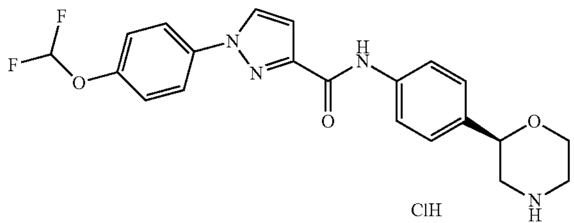 [SMILES: O=C(Nc1ccc([C@@H]2CNCCO2)cc1)c1ccn(-c2ccc(OC(F)F)cc2)n1 ; Cl]

The title compound was obtained in analogy to example 45 using (R)-tert-butyl 2-(4-aminophenyl)morpholine-4-carboxylate instead of (S)-tert-butyl 2-(4-aminophenyl)morpholine-4-carboxylate in step c). Off-white solid. MS (ISP): 415.4 ($[M+H]^+$).

Example 47

(S)—N-(4-(Morpholin-2-yl)phenyl)-1-(5-(trifluoromethyl)pyrimidin-2-yl)-1H-pyrazole-3-carboxamide hydrochloride

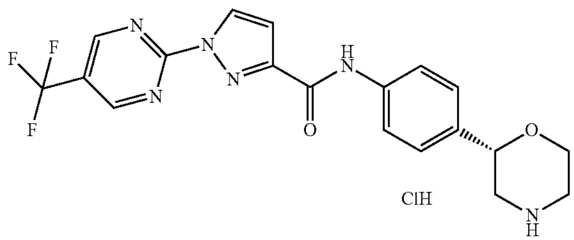 [SMILES: O=C(Nc1ccc([C@H]2CNCCO2)cc1)c1ccn(-c2ncc(C(F)(F)F)cn2)n1 ; Cl]

a) (S)-tert-Butyl 2-(4-(1H-pyrazole-3-carboxamido)phenyl)morpholine-4-carboxylate 1H-Pyrazole-3-carboxylic acid (560 mg, 5 mmol) was dissolved in methanol (62 ml) and (S)-tert-butyl 2-(4-aminophenyl)morpholine-4-carboxylate (1.39 g, 5 mmol) was added. The solution was cooled to 0° C. and 4-(4,6-dimethoxy-1,3,5-triazin-2-yl)-4-methylmorpholinium chloride (1.8 g, 6.5 mmol) dissolved in 5 ml methanol was added drop-wise to the reaction mixture in 1 hour. The reaction mixture was stirred at 0° C. for two hours then overnight at room temperature. The solvent was evaporated, the residue was dissolved in dichloromethane and adsorbed on silicagel.

The material was purified by flash chromatography (silica gel, 20 g, 30% to 50% EtOAc in heptane) to yield a white solid (1.61 g; 86%) which was used for the next step.

b) (S)-tert-Butyl 2-(4-(1-(5-(trifluoromethyl)pyrimidin-2-yl)-1H-pyrazole-3-carboxamido)phenyl)morpholine-4-carboxylate (S)-tert-Butyl 2-(4-(1H-pyrazole-3-carboxamido)phenyl)morpholine-4-carboxylate (33 mg, 0.089 mmol) and 2-chloro-5-(trifluoromethyl)pyrimidine (16.2 mg, 0.089 mmol) were dissolved in DMSO (0.7 ml) and potassium carbonate (24.5 mg, 0.177 mmol) was added. The reaction mixture was placed on a Büchi shaker for 20 hours at 120° C. After cooling the mixture, water was added followed by extraction with ethyl acetate twice. The combined organic layers were dried over MgSO4 and evaporated. The crude material was purified by flash chromatography (silica gel, 5 g, 25% to 50% EtOAc in heptane) to yield an off-white solid (11 mg, 24%). MS (ISP): 463.1 (100%, $[M-tBu+H]^+$), 519.3 (10%, $[M+H]^+$).

c) (S)—N-(4-(Morpholin-2-yl)phenyl)-1-(4-(trifluoromethoxy)phenyl)-1H-pyrazole-4-carboxamide hydrochloride (S)-tert-Butyl 2-(4-(1-(5-(trifluoromethyl)pyrimidin-2-yl)-1H-pyrazole-3-carboxamido)phenyl)morpholine-4-carboxylate (11 mg, 21.2 μmol) was dissolved in dioxane (80 μL) and a solution of HCl in dioxane (79.6 μL, 318 μmol) was added and the reaction mixture was stirred at 60° C. for 2 hours. After cooling, diethylether was added and the solid was filtered and washed with diethylether to afford (S)—N-(4-(morpholin-2-yl)phenyl)-1-(4-(trifluoromethoxy)phenyl)-1H-pyrazole-4-carboxamide hydrochloride (7 mg, 70%) as an off-white solid. MS (ISP): 419.3 ($[M+H]^+$).

Example 48

(S)-1-(6-Chloropyrazin-2-yl)-N-(4-(morpholin-2-yl)phenyl)-1H-pyrazole-3-carboxamide hydrochloride

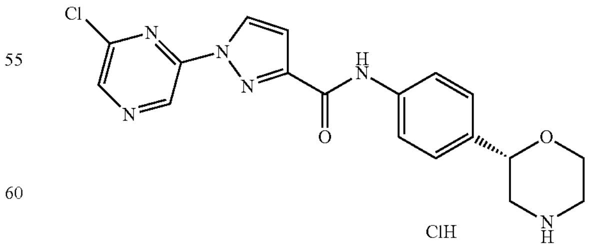

The title compound was obtained in analogy to example 47 using 2,6-dichloropyrazine instead of 2-chloro-5-(trifluoromethyl)pyrimidine in step b). Yellow solid. MS (ISP): 385.3 ($[\{^{35}Cl\}M+H]^+$), 387.3 ($[\{^{37}Cl\}M+H]^+$). ($[M+H]^+$).

Example 49

(S)-1-(3-Chloropyrazin-2-yl)-N-(4-(morpholin-2-yl)phenyl)-1H-pyrazole-3-carboxamide hydrochloride

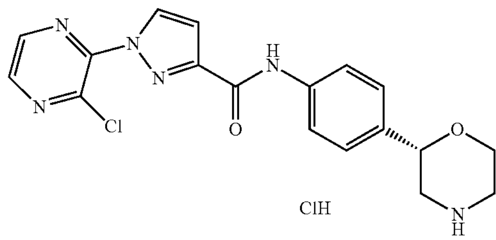 [SMILES: O=C(Nc1ccc([C@H]2CNCCO2)cc1)c1ccn(-c2nccnc2Cl)n1 ; Cl]

a) (S)-tert-Butyl 2-(4-(1-(3-chloropyrazin-2-yl)-1H-pyrazole-3-carboxamido)phenyl)morpholine-4-carboxylate (S)-tert-Butyl 2-(4-(1H-pyrazole-3-carboxamido)phenyl)morpholine-4-carboxylate (90 mg, 0.24 mmol) and 2,3-dichloropyrazine (43 mg, 0.29 mmol) were dissolved in dimethylacetamide (2 ml) and potassium carbonate (67 mg, 0.48 mmol) was added. The reaction mixture was placed on a Büchi shaker for 16 hours at 80° C. To complete the reaction an additional amount of 2,3-dichloropyrazine (10 mg) was added and heating was continued for another 2 h at 120° C. After cooling the mixture, water was added followed by extraction with ethyl acetate twice. The combined organic layers was dried over MgSO4 and evaporated. The crude material was purified by flash chromatography (silica gel, 10 g, 25% to 50% EtOAc in heptane) to yield an off-white gum (48 mg, 42%). MS (ISP): 429.3 (100%, $[M-tBu+H]^+$), 485.4 (10%, $[M+H]^+$).

b) (S)-1-(3-Chloropyrazin-2-yl)-N-(4-(morpholin-2-yl)phenyl)-1H-pyrazole-3-carboxamide hydrochloride (S)-tert-Butyl 2-(4-(1-(3-chloropyrazin-2-yl)-1H-pyrazole-3-carboxamido)phenyl)morpholine-4-carboxylate (44 mg, 90.7 μmol) was dissolved in dioxane (0.35 ml) and a solution of HCl in dioxane (340 μl, 1.36 mmol) was added and the reaction mixture was stirred at 60° C. for 90 min.

The solvent was evaporated and the residue was recrystallized from a mixture of ethyl acetate and ethanol to yield a light yellow solid (27 mg, 70%). MS (ISP): 385.2 ($[\{^{35}Cl\}M+H]^+$), 387.2 ($[\{^{37}Cl\}M+H]^+$). ($[M+H]^+$).

Example 50

(S)-1-(5-Chloropyrazin-2-yl)-N-(4-(morpholin-2-yl)phenyl)-1H-pyrazole-3-carboxamide hydrochloride

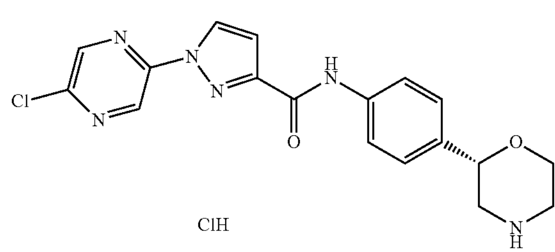 [SMILES: O=C(Nc1ccc([C@H]2CNCCO2)cc1)c1ccn(-c2cnc(Cl)cn2)n1 ; Cl]

The title compound was obtained in analogy to example 49 using 2,5-dichloropyrazine instead of 2,3-dichloropyrazine in step a). Off-white solid. MS (ISP): 385.2 ($[\{^{35}Cl\}M+H]^+$), 387.2 ($[\{^{37}Cl\}M+H]^+$). ($[M+H]^+$).

Example 51

(S)—N-(4-(Morpholin-2-yl)phenyl)-1-(6-(trifluoromethyl)pyrimidin-4-yl)-1H-pyrazole-3-carboxamide hydrochloride

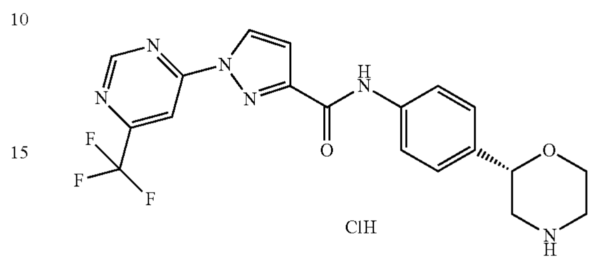

The title compound was obtained in analogy to example 49 using 4-chloro-6-(trifluoromethyl)pyrimidine instead of 2,3-dichloropyrazine in step a). White solid. MS (ISP): 419.2 ($[M+H]^+$).

Example 52

(S)—N-(4-(Morpholin-2-yl)phenyl)-1-(6-(trifluoromethyl)pyrazin-2-yl)-1H-pyrazole-3-carboxamide hydrochloride

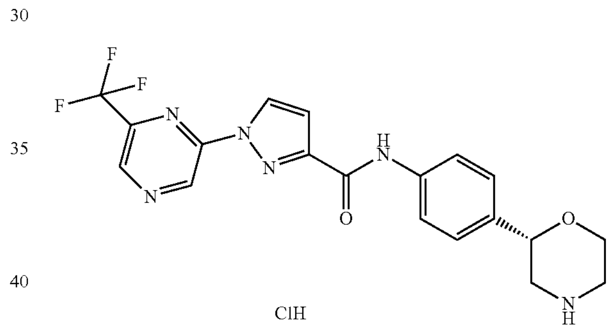

The title compound was obtained in analogy to example 49 using 2-iodo-6-(trifluoromethyl)pyrazine instead of 2,3-dichloropyrazine in step a). Light yellow solid. MS (ISP): 419.2 ($[M+H]^+$).

Example 53

(S)-1-(5-Cyanopyrazin-2-yl)-N-(4-(morpholin-2-yl)phenyl)-1H-pyrazole-3-carboxamide hydrochloride

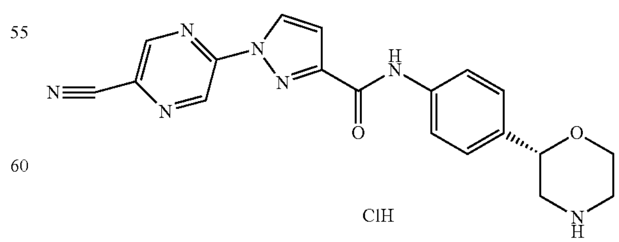

The title compound was obtained in analogy to example 49 using 5-bromopyrazine-2-carbonitrile instead of 2,3-dichloropyrazine in step a). Light yellow solid. MS (ISP): 376.3 ($[M+H]^+$).

Example 54

(S)—N-(4-(Morpholin-2-yl)phenyl)-1-(2-(trifluoromethyl)pyrimidin-4-yl)-1H-pyrazole-3-carboxamide hydrochloride

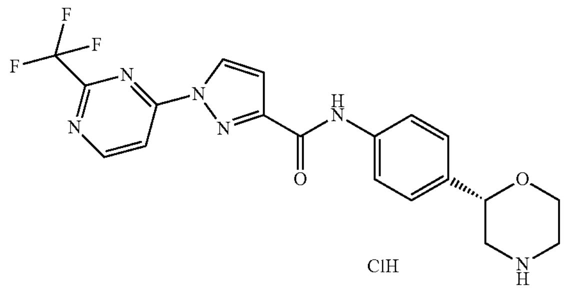 [SMILES: O=C(Nc1ccc([C@H]2CNCCO2)cc1)c1ccn(-c2ccnc(C(F)(F)F)n2)n1 ; Cl]

The title compound was obtained in analogy to example 49 using 4-chloro-2-(trifluoromethyl)pyrimidine instead of 2,3-dichloropyrazine in step a). Light green solid. MS (ISP): 419.2 ([M+H]$^+$).

The compounds of formula I and their pharmaceutically usable addition salts possess valuable pharmacological properties. Specifically, the compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Radioligand Binding Assay on rat TAAR1

Membrane Preparation and Radioligand Binding.

HEK-293 cells stably expressing rat TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve.

The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated Kd value, that was usually around 2.3 nM, resulting in the binding of approximately 0.2% of the radioligand and a specific binding representing approximately 85% of the total binding. Nonspecific binding was defined as the amount of $^3$-[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]—(S)-4-[(ethyl-phenyl-amino)-methyl]-4,5-dihydro-oxazol-2-ylamine at a concentration of 3.3×Kd in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

Radioligand Binding Assay on Mouse TAAR1

Membrane Preparation and Radioligand Binding.

HEK-293 cells stably expressing mouse TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3$[H]—

(S)-4-[(ethyl-phenyl-amino)-methyl]-4,5-dihydro-oxazol-2-ylamine (described in WO 2008/098857) was used at a concentration equal to the calculated Kd value, that was usually around 0.7 nM, resulting in the binding of approximately 0.5% of the radioligand and a specific binding representing approximately 70% of the total binding. Nonspecific binding was defined as the amount of $^{3}$[H]—(S)-4-[(ethyl-phenyl-amino)-methyl]-4,5-dihydro-oxazol-2-ylamine bound in the presence of 10 μM unlabeled ligand. All compounds were tested at a broad range of concentrations (10 μM to 10 μM) in duplicates. The test compounds (20 μl/well) were transferred into a 96 deep well plate (TreffLab), and 180 μl of HEPES-NaOH (20 mM, pH 7.4) containing $MgCl_2$ (10 mM) and $CaCl_2$ (2 mM) (binding buffer), 300 μl of the radioligand $^{3}$[H]—(S)-4-[(ethyl-phenyl-amino)-methyl]-4,5-dihydro-oxazol-2-ylamine at a concentration of 3.3× Kd in nM and 500 μl of the membranes (resuspended at 60 μg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 μl of Microscint 40 (PerkinElmer) the Unifilter-96 plate was sealed and after 1 hr the radioactivity counted using a TopCount Microplate Scintillation Counter (Packard Instrument Company).

The compounds show a Ki value (μM) in mouse or rat on TAAR1 in the range of <0.1 μM as shown in the table below.

| Example | Ki (μM) mouse/rat |
|---|---|
| 1 | 0.0007/0.0043 |
| 2 | 0.0003/0.0004 |
| 3 | 0.0008/0.0027 |
| 4 | 0.001/0.0022 |
| 5 | 0.0072/0.0045 |
| 6 | 0.0016/0.008 |
| 7 | 0.0012/0.0049 |
| 8 | 0.0009/0.0073 |
| 9 | 0.0014/0.014 |
| 10 | 0.0005/0.0026 |
| 11 | 0.0026/0.0127 |
| 12 | 0.0005/0.0004 |
| 13 | 0.0008/0.001 |
| 14 | 0.0017/0.0028 |
| 15 | 0.0006/0.0004 |
| 16 | 0.0013/0.0014 |
| 17 | 0.0016/0.0024 |
| 18 | 0.0017/0.0254 |
| 19 | 0.0079/0.0028 |
| 20 | 0.0022/0.0074 |
| 21 | 0.0053/0.0055 |
| 22 | 0.0023/0.0022 |
| 23 | 0.0064/0.0088 |
| 24 | 0.0067/0.0142 |
| 25 | 0.0051/0.0078 |
| 26 | 0.0734/0.0316 |
| 27 | 0.0021/0.0135 |
| 28 | 0.0043/0.0129 |
| 29 | 0.0011/0.0024 |
| 30 | 0.1428/1.3212 |
| 31 | 0.0013/0.0024 |
| 32 | 0.0007/0.0011 |
| 33 | 0.0028/0.0016 |
| 34 | 0.0037/0.0092 |
| 35 | 0.0022/0.0006 |
| 36 | 0.0014/0.0138 |
| 37 | 0.0017/0.0027 |
| 38 | 0.0021/0.0042 |
| 39 | 0.0014/0.003 |
| 40 | 0.0005/0.0013 |
| 41 | 0.0025/0.0016 |
| 42 | 0.001/0.0021 |
| 43 | 0.0016/0.011 |
| 44 | 0.0663/0.0262 |
| 45 | 0.0018/0.0014 |
| 46 | 0.004/0.0006 |
| 47 | 0.0198/0.0196 |
| 48 | 0.0086/0.0118 |
| 49 | 0.0142/0.139 |
| 50 | 0.0027/0.0091 |
| 51 | 0.0142/0.0071 |
| 52 | 0.0084/0.0074 |
| 53 | 0.011/0.0298 |
| 54 | 0.0065/0.0088 |

The compounds of formula IA and IB and the pharmaceutically acceptable salts of the compounds of formula IA and IB can be used as therapeutics, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula IA and IB can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula IA or IB or a pharmaceutically acceptable salt thereof and a therapeutically inert carrier are also an embodiment of the present invention, as is a process for their production, which comprises bringing one or more compounds of formula IA or IB and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety and attention deficit hyperactivity disorder (ADHD) and diabetes.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The invention claimed is:

1. A compound of formula IA or IB

IA

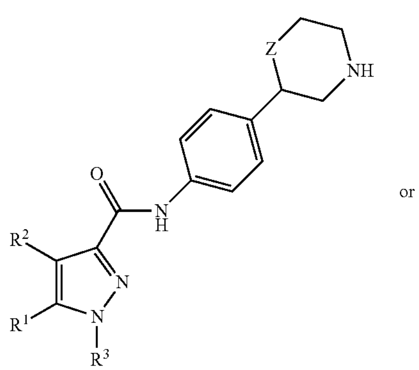

or

-continued

IB

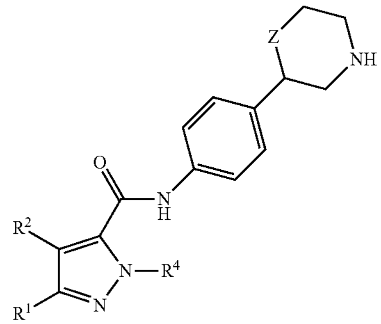

wherein $R^1$ is hydrogen,
phenyl substituted by halogen, CN, lower alkoxy or lower alkoxy substituted by halogen;

$R^2$ is hydrogen or lower alkyl;

$R^3$ is hydrogen,
lower alkyl,
phenyl substituted by one or more substituents selected from halogen, cyano and lower alkoxy substituted by halogen,
pyridinyl optionally substituted by halogen or lower alkyl substituted by halogen, pyrimidinyl optionally substituted by lower alkyl substituted by halogen, or pyrazinyl optionally substituted by halogen, cyano or lower alkyl substituted by halogen;

$R^4$ is hydrogen, lower alkyl or phenyl; and

Z is a bond, —$CH_2$— or —O—;

or a pharmaceutically suitable acid addition salt thereof.

2. The compound of claim 1, having formula IA-2,

IA-2

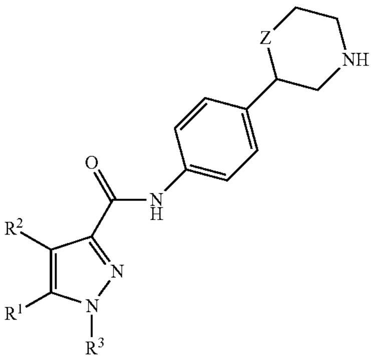

$R^1$ is hydrogen;

$R^2$ is hydrogen or lower alkyl;

$R^3$ is phenyl substituted by one or more substituents selected from halogen, cyano and lower alkoxy substituted by halogen,
pyridinyl optionally substituted by halogen or lower alkyl substituted by halogen, pyrimidinyl optionally substituted by lower alkyl substituted by halogen, or pyrazinyl optionally substituted by halogen, cyano or lower alkyl substituted by halogen; and Z is a bond, —$CH_2$— or —O—;

or a pharmaceutically suitable acid addition salt thereof.

3. The compound of claim 2, selected from the group consisting of (S)—N-(4-(morpholin-2-yl)phenyl)-1-(5-(trifluoromethyl)pyrimidin-2-yl)-1H-pyrazole-3-carboxamide;
(S)-1-(6-chloropyrazin-2-yl)-N-(4-(morpholin-2-yl)phenyl)-1H-pyrazole-3-carboxamide;
(S)-1-(3-chloropyrazin-2-yl)-N-(4-(morpholin-2-yl)phenyl)-1H-pyrazole-3-carboxamide;
(S)-1-(5-chloropyrazin-2-yl)-N-(4-(morpholin-2-yl)phenyl)-1H-pyrazole-3-carboxamide;
(S)—N-(4-(morpholin-2-yl)phenyl)-1-(6-(trifluoromethyl)pyrimidin-4-yl)-1H-pyrazole-3-carboxamide;
(S)—N-(4-(morpholin-2-yl)phenyl)-1-(6-(trifluoromethyl)pyrazin-2-yl)-1H-pyrazole-3-carboxamide;
(S)-1-(5-cyanopyrazin-2-yl)-N-(4-(morpholin-2-yl)phenyl)-1H-pyrazole-3-carboxamide and
(S)—N-(4-(morpholin-2-yl)phenyl)-1-(2-(trifluoromethyl)pyrimidin-4-yl)-1H-pyrazole-3-carboxamide.

4. A pharmaceutical composition comprising a therapeutically effective amount of a compound of formula IA or IB

IA

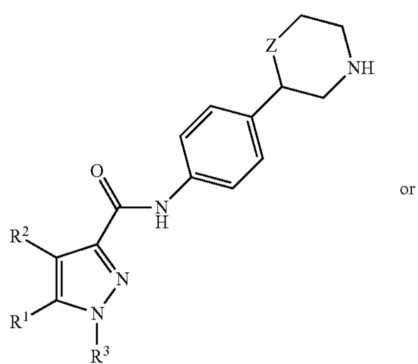

or

-continued

IB

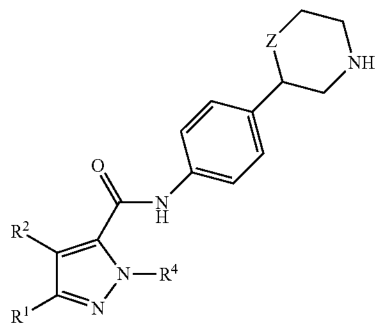

wherein $R^1$ is hydrogen,
phenyl substituted by halogen, CN, lower alkoxy or lower alkoxy substituted by halogen;

$R^2$ is hydrogen or lower alkyl;

$R^3$ is hydrogen,
lower alkyl,
phenyl substituted by one or more substituents selected from halogen, cyano and lower alkoxy substituted by halogen,
pyridinyl optionally substituted by halogen or lower alkyl substituted by halogen, pyrimidinyl optionally substituted by lower alkyl substituted by halogen, or pyrazinyl optionally substituted by halogen, cyano or lower alkyl substituted by halogen;

$R^4$ is hydrogen, lower alkyl or phenyl; and

Z is a bond, —$CH_2$— or —O—;

or a pharmaceutically suitable acid addition salt thereof and a pharmaceutically acceptable carrier.

* * * * *